US012642512B2

(12) United States Patent
Vaid et al.

(10) Patent No.:  US 12,642,512 B2
(45) Date of Patent:    Jun. 2, 2026

(54) SURFACING INSIGHTS INTO LEFT AND RIGHT VENTRICULAR DYSFUNCTION THROUGH DEEP LEARNING

(71) Applicant: Icahn School of Medicine at Mount Sinai, New York, NY (US)

(72) Inventors: Akhil Vaid, New York, NY (US); Girish N. Nadkarni, New York, NY (US); Benjamin S. Glicksberg, New York, NY (US)

(73) Assignee: Icahn School of Medicine at Mount Sinai, New York, NY (US)

( * ) Notice:    Subject to any disclaimer, the term of this patent is extended or adjusted under 35 U.S.C. 154(b) by 9 days.

(21) Appl. No.: 18/821,043

(22) Filed:    Aug. 30, 2024

(65)            Prior Publication Data

US 2025/0127493 A1      Apr. 24, 2025

Related U.S. Application Data

(63) Continuation of application No. 17/714,060, filed on Apr. 5, 2022, now Pat. No. 12,102,485.

(51) Int. Cl.
     *A61B 8/00*            (2006.01)
     *A61B 8/06*            (2006.01)
                    (Continued)

(52) U.S. Cl.
     CPC ............ *A61B 8/5284* (2013.01); *A61B 8/065* (2013.01); *A61B 8/5223* (2013.01); *G16H 10/60* (2018.01); *G16H 15/00* (2018.01); *G16H 50/20* (2018.01)

(58) Field of Classification Search
     CPC ..... A61B 8/5284; A61B 8/065; A61B 8/5223; A61B 8/0883; G16H 10/60; G16H 15/00; G16H 50/20; G16H 50/70
     See application file for complete search history.

(56)            References Cited

U.S. PATENT DOCUMENTS

|              |        |         |              |
|--------------|--------|---------|--------------|
| 10,362,949 B2 * | 7/2019 | Beymer | ............... A61B 5/7425 |
| 2005/0020903 A1 * | 1/2005 | Krishnan | ............... G16H 50/20 |
|              |        |         | 600/407      |

(Continued)

OTHER PUBLICATIONS

Jin-Yu Sun et al: "A method to screen left ventricular dysfunction through ECG based on convolutional neural network", Journal of Cardiovascular Electrophysiology, Futura Publishing Co., Armonk, NY, US, vol. 32, No. 4, Feb. 15, 2021 (Feb. 15, 2021), pp. 1095-1102, XP071951712, ISSN: 1045-3873, DOI: 10.1111/JCE.14936 * the whole document*.

(Continued)

*Primary Examiner* — Bo Joseph Peng
(74) *Attorney, Agent, or Firm* — Leason Ellis LLP

(57)            ABSTRACT

Introduced here approaches to developing, training, and implementing algorithms to cardiac dysfunction through automated analysis of physiological data. As an example, a model may be developed and then trained to quantify left and right ventricular dysfunction using electrocardiogram waveform data that is associated with a population of individuals who are diverse in terms of age, gender, ethnicity, socioeconomic status, and the like. This approach to training allows the model to predict the presence of left and right ventricular dysfunction in a diverse population. Also introduced here is a regression framework for predicting numeric values of left ventricular ejection fraction.

19 Claims, 31 Drawing Sheets

300

301
Receive input indicative of a selection of (i) a first dataset that is representative of information generated as part of a plurality of transthoracic echocardiograms involving a first plurality of patients and (ii) a second dataset that is representative of information generated as part of a plurality of electrocardiograms involving a second plurality of patients 302
Establish outcomes of the plurality of transthoracic echocardiograms based on an analysis of the first dataset 303
Identify echocardiogram-electrocardiogram pairs by pairing the plurality of transthoracic echocardiograms with the plurality of electrocardiograms, such that each transthoracic echocardiogram is paired with electrocardiograms, if any, that occurred within a predetermined amount of time 304
Provide the echocardiogram-electrocardiogram pairs and corresponding outcomes to a neural network as training data, so as to produce a trained neural network that is able to stratify patients among the outcomes 305
Store the trained neural network in a data structure

(51) Int. Cl.

| | | |
|---|---|---|
| *G16H 10/60* | (2018.01) | |
| *G16H 15/00* | (2018.01) | |
| *G16H 50/20* | (2018.01) | |

(56) References Cited

U.S. PATENT DOCUMENTS

| | | | | | |
|---|---|---|---|---|---|
| 2011/0021933 | A1 | 1/2011 | Radzievsky et al. | | |
| 2014/0052001 | A1 | 2/2014 | Ionasec et al. | | |
| 2014/0074509 | A1* | 3/2014 | Amarasingham | ...... | G16H 50/70 |
| | | | | | 705/3 |
| 2018/0103931 | A1* | 4/2018 | Negahdar | ............ | A61B 8/5223 |
| 2018/0107787 | A1* | 4/2018 | Compas | ............ | G06F 18/24143 |
| 2018/0107791 | A1* | 4/2018 | Guo | ........................ | G06Q 40/08 |
| 2018/0107792 | A1* | 4/2018 | Rajan | ...................... | G16H 50/20 |
| 2018/0107801 | A1* | 4/2018 | Guo | .................... | G06F 16/9035 |
| 2019/0183431 | A1* | 6/2019 | Attia | .................... | G06N 3/0464 |
| 2020/0315527 | A1* | 10/2020 | Neumann | ............ | A61B 5/4842 |
| 2020/0321113 | A1* | 10/2020 | Neumann | .............. | G06N 20/00 |
| 2020/0321122 | A1* | 10/2020 | Neumann | .............. | G16B 20/00 |
| 2020/0397313 | A1* | 12/2020 | Attia | ...................... | G16H 40/67 |
| 2021/0059540 | A1 | 3/2021 | Peterson et al. | | |
| 2023/0420132 | A1* | 12/2023 | Pahlevan | .............. | G16H 50/20 |

OTHER PUBLICATIONS

Partial Supplementary European Search Report in EP Application No. 23785283.5-1122/4504067, mailed Jun. 10, 2025 (14 pages).

International Search Report and Written Opinion mailed Aug. 14, 2023 for International Patent Application No. PCT/US23/17469, 11 pages.

Vaid, Akhil, et al., "Using Deep Learning Algorithms to Simultaneously Identify Right and Left Ventricular Dysfunction From the Electrocardiogram", JACC: Cardiovascular Imaging, vol. 15, No. 3, Mar. 2022.

* cited by examiner

100

106

108A

Computing Device 104

Diagnostic Platform 102

108B

110

Figure 3:
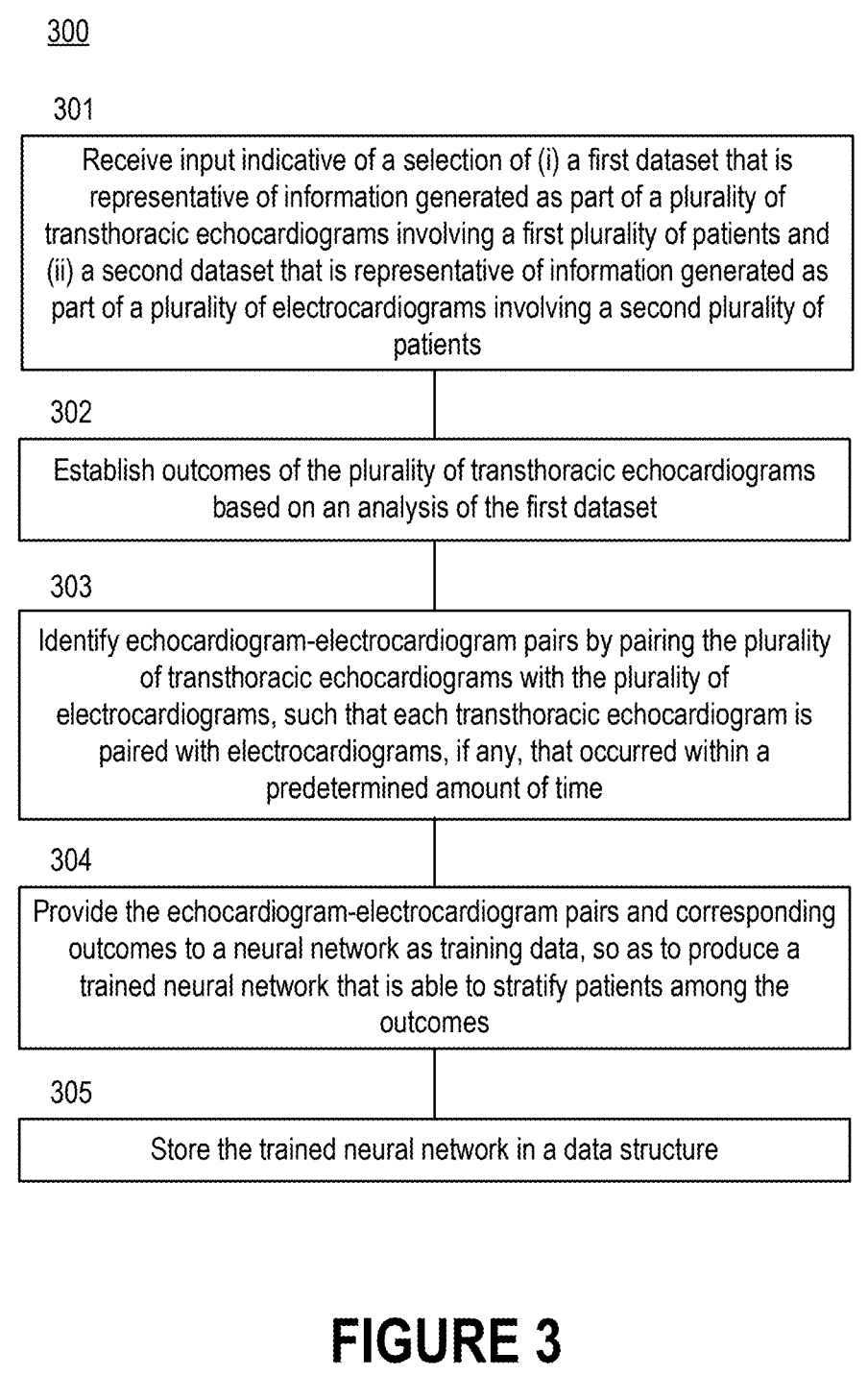

300

301

Receive input indicative of a selection of (i) a first dataset that is representative of information generated as part of a plurality of transthoracic echocardiograms involving a first plurality of patients and (ii) a second dataset that is representative of information generated as part of a plurality of electrocardiograms involving a second plurality of patients

302

Establish outcomes of the plurality of transthoracic echocardiograms based on an analysis of the first dataset

303

Identify echocardiogram-electrocardiogram pairs by pairing the plurality of transthoracic echocardiograms with the plurality of electrocardiograms, such that each transthoracic echocardiogram is paired with electrocardiograms, if any, that occurred within a predetermined amount of time

304

Provide the echocardiogram-electrocardiogram pairs and corresponding outcomes to a neural network as training data, so as to produce a trained neural network that is able to stratify patients among the outcomes

305

Store the trained neural network in a data structure

Figure 4:
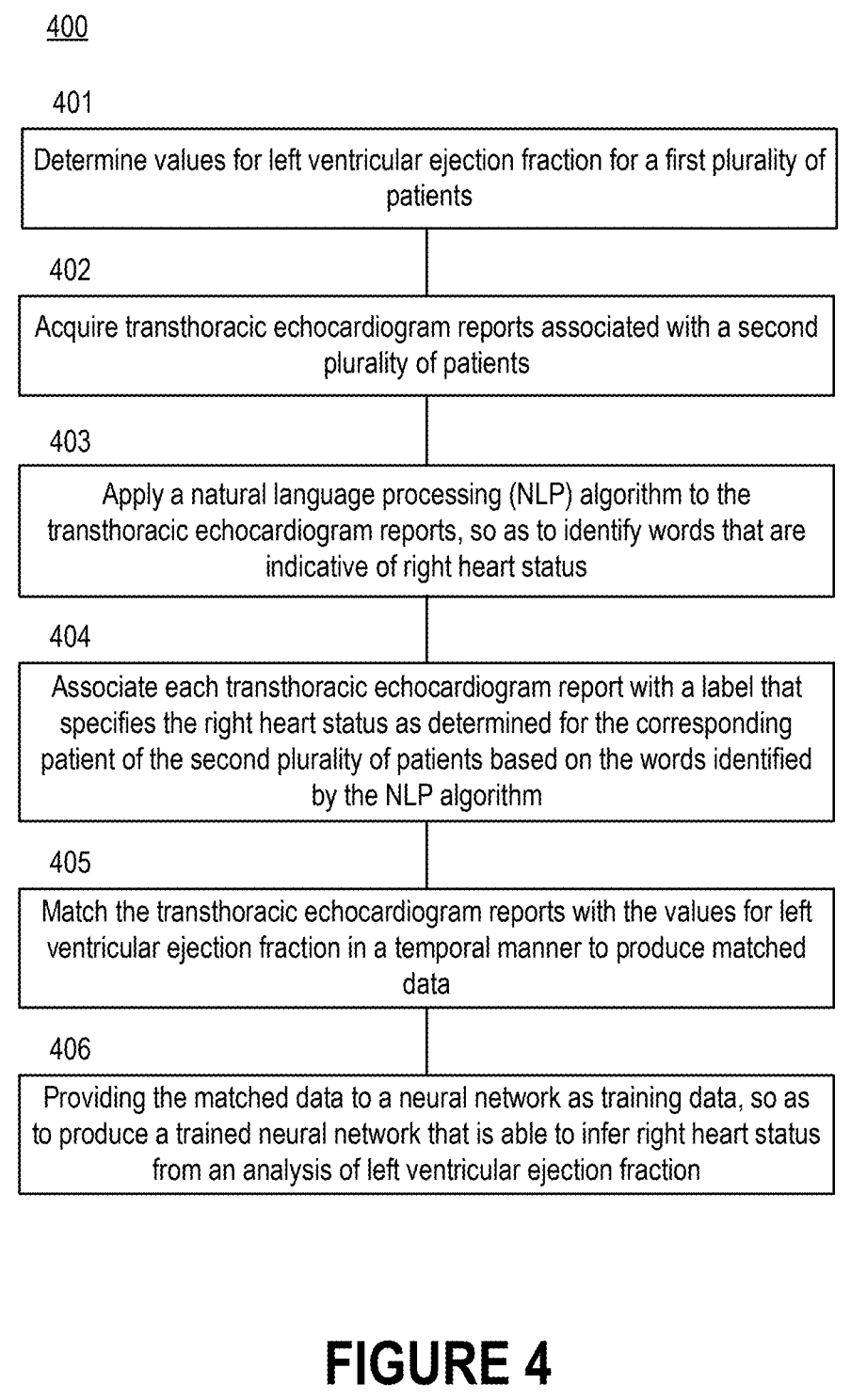

| Determine values for left ventricular ejection fraction for a first plurality of patients |
|---|

402

| Acquire transthoracic echocardiogram reports associated with a second plurality of patients |
|---|

403

| Apply a natural language processing (NLP) algorithm to the transthoracic echocardiogram reports, so as to identify words that are indicative of right heart status |
|---|

404

| Associate each transthoracic echocardiogram report with a label that specifies the right heart status as determined for the corresponding patient of the second plurality of patients based on the words identified by the NLP algorithm |
|---|

405

| Match the transthoracic echocardiogram reports with the values for left ventricular ejection fraction in a temporal manner to produce matched data |
|---|

406

| Providing the matched data to a neural network as training data, so as to produce a trained neural network that is able to infer right heart status from an analysis of left ventricular ejection fraction |
|---|

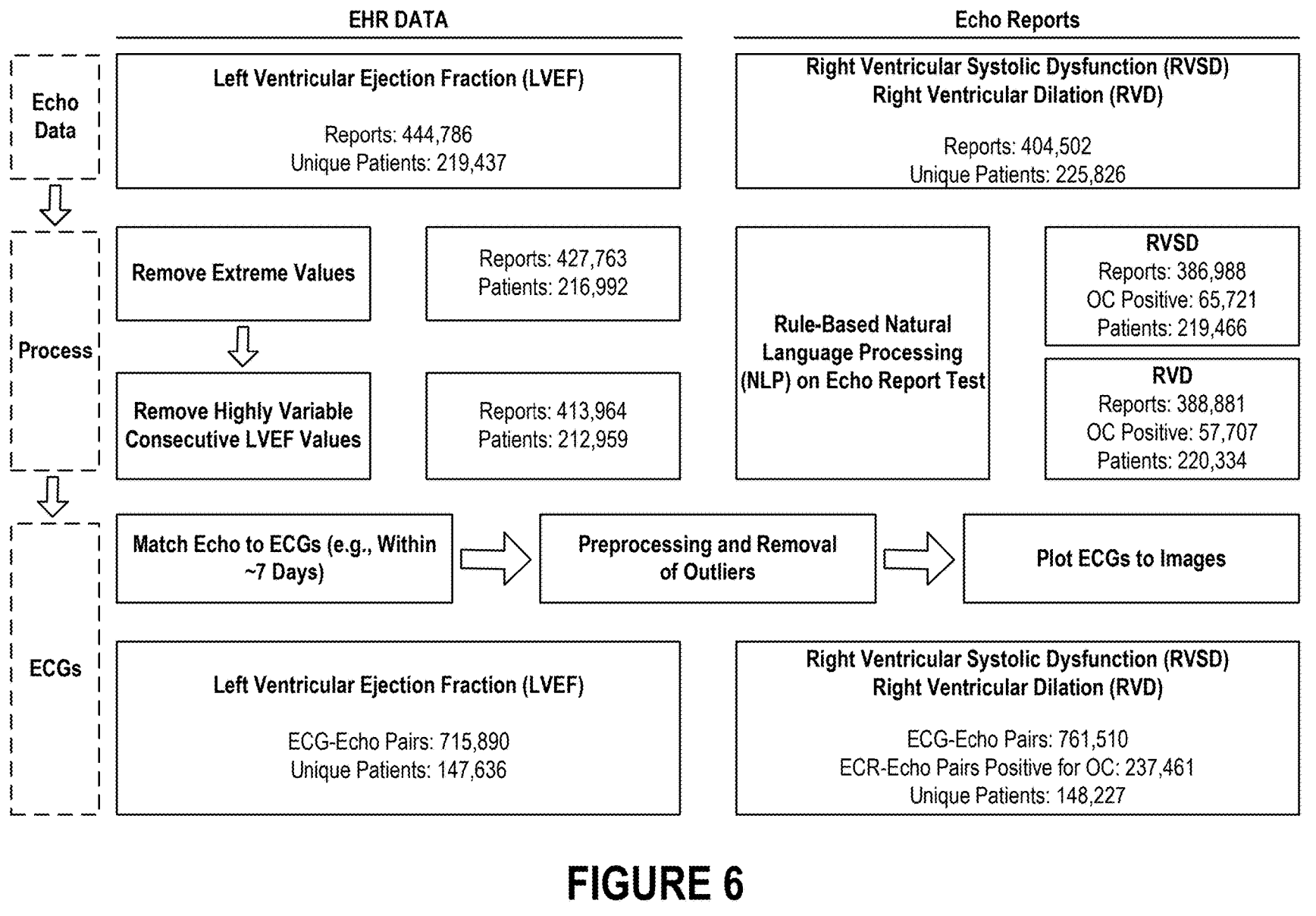

Echo Reports

Right Ventricular Systolic Dysfunction (RVSD)
Right Ventricular Dilation (RVD)

Reports: 404,502
Unique Patients: 225,826

RVSD
Reports: 386,988
OC Positive: 65,721
Patients: 219,466

RVD
Reports: 388,881
OC Positive: 57,707
Patients: 220,334

Plot ECGs to Images

Right Ventricular Systolic Dysfunction (RVSD)
Right Ventricular Dilation (RVD)

ECG-Echo Pairs: 761,510
ECR-Echo Pairs Positive for OC: 237,461
Unique Patients: 148,227

Rule-Based Natural Language Processing (NLP) on Echo Report Test

Preprocessing and Removal of Outliers

EHR DATA

Left Ventricular Ejection Fraction (LVEF)

Reports: 444,786
Unique Patients: 219,437

Reports: 427,763
Patients: 216,992

Reports: 413,964
Patients: 212,959

Remove Extreme Values

Remove Highly Variable Consecutive LVEF Values

Match Echo to ECGs (e.g., Within ~7 Days)

Left Ventricular Ejection Fraction (LVEF)

ECG-Echo Pairs: 715,890
Unique Patients: 147,636

Echo Data

Process

ECGs

FIGURE 6

ANONYMIZED

PROCEDURE(S) Complete two-dimensional echocardiogram (TTE) Color-flow imaging Complete Doppler ; DIAGNOSES . heart murmur, unspecified, Unspecified atrial fibrillation REASON(S) FOR TESTING : evaluate valves and ventricular function CONCLUSIONS : normal left ventricular size normal left ventricular systolic function; ejection fraction = 65 % mild to moderate concentric left ventricular hypertrophy normal right ventricular size RV NORMAL SIZE normal right ventricular function RV NORMAL FUNCTION severe valvular aortic stenosis mild aortic regurgitation, severity may be under estimated moderate mitral regurgitation MV REGURGITATION mild to moderate tricuspid regurgitation moderate pulmonary hypertension no evidence for pericardial effusion technically difficult study ANONYMIZED Left Ventricle : abnormal left ventricular diastolic filling pattern (may be due to age or LVH); LV diastolic function measurements: MV-e =0.86 m/sec, DTI-e = 0.07 m/sec, E/e' = 12.29, MV deceleration time = 183 msec no left ventricular outflow tract obstruction mild to moderate concentric left ventricular hypertrophy, more in basal anteroseptal wall; LV mass = 279 g, LV mass index=173.29 g/m2, 166.07 g/m(ht), 68.75 g/m^2.7(ht)* normal left ventricular systolic function; ejection fraction = 65 % normal left ventricular size; LVIDd = 4.7 cm Right Ventricle : normal right ventricular function RV NORMAL FUNCTION normal right ventricular size RV NORMAL SIZE Left Atrium : moderate left atrial dilatation ; area-4ch = 30 cm2, length-4ch = 8 cm Right Atrium : normal inferior vena cava; size = 1.9 cm, no change with respiration or sniff mild right atrial dilatation ; area 4-ch = 21 cm2 Aortic Valve : mild aortic regurgitation, severity may be under estimated severe valvular aortic stenosis; peak gradient = 81 mmHg, mean gradient = 58 mmHg, Doppler valve area = 0.62 sq cm, LVOT diameter = 2.2 cm, LVOT peak pulsed velocity = 0.73 m/sec, Ao peak CW velocity = 4.5 m/sec, Doppler valve area by VTI= 0.52 sq cm, LVOT pulsed velocity VTI = 0.17 m/sec, Ao CW velocity VTI = 1.25 m/sec Mitral Valve : no evidence for inflow obstruction due to mitral annular/ valvular fibrocalcification mitral annular fibrocalcification fibrocalcification of mitral valve chordae mitral valve thickening moderate mitral regurgitation MV REGURGITATION Tricuspid Valve : moderate pulmonary hypertension; peak CW velocity = 3.6 m/sec, peak gradient = 52 mmHg, estimated RA pressure = 5 mmHg, RV sys. pressure = 57 mmHg mild to moderate tricuspid regurgitation Pulmonic Valve : mild pulmonic regurgitation, severity may be over estimated Pericardium : no evidence for pericardial effusion Aorta : normal sinus of valsalva dimension; diameter = 3.5 cm Miscellaneous : technically difficult study Detailed Findings Rest ECG : Rhythm : atrial fibrillation * = number or calculation differs from reader's assessment ANONYMIZED Ht. : Wt. : BSA : 66.00 in 119.00 lbs 1.61 m2 HR : BP : 59 /min 160/77 mmHg (Before) 2-D Guided Measurement and Calculations Normal Ranges Linear Left Ventricle IV Septum-thickness Diastole (SWTd) 1.5 cm 0.8 -1.1 cm LV Posterior wall-thickness Diastole (PWTd) 1.4 cm 0.8 - 1.1 cm Dimensions (A. S. E.) Diastole (Dd) 4.7 cm Systole (Ds) 3.1 cm Calculated values Fractional shortening 34 % End-diastolic volume 102 61 mL 50 - 90 mL/m2 End-systolic volume 38 23 mL 30 - 70 mL/m2 Stroke volume 64 38 mL Ejection fraction 63 % 55 - 70 % * A. S. E. : Measurement technique according to American Society of Echocardiography Apical 2-D measurements and calculations of left ventricle 4-chamber 2-chamber Biplane End-diastolic volume 110 104 mL mL End-systolic volume 38 40 mL mL Stroke volume 72 64 mL mL Ejection fraction 65 62 % % Page 3 of 3

FIGURE 7A

[ANONYMIZED]

PROCEDURE(S) Complete two-dimensional echocardiogram (TTE) Color-flow Imaging Complete Doppler ; DIAGNOSES : s/p mitral valve replacement REASON(S) FOR TESTING : evaluate valves and ventricular function CONCLUSIONS ; Abnormal Mitral Tissue Prosthesis: partially obstructed and high gradient; cannot exclude fibrocalcification, partial thrombosis or vegetation ; suggest TEE normal left ventricular size moderate concentric left ventricular hypertrophy overall moderate decreased left ventricular systolic function (segmental); ejection fraction = 28 % LV function varies with R-R interval mild left atrial dilatation [minimal mitral regurgitation MV: BORDERLINE REGURGITATION] mild to moderate tricuspid regurgitation moderate pulmonary hypertension study performed with patient supine mild to moderate [decreased right ventricular function RV: ABNORMAL FUNCTION] mild [right ventricular dilatation RV: ABNORMAL SIZE] technically difficult study Definity® precision microbubble contrast used to enhance endocardial border definition

[ANONYMIZED] Left Ventricle : LV function varies with R-R interval moderate concentric left ventricular hypertrophy; LV mass = 271 g, LV mass index = 167.38 g/m2, 169.38 g/m(ht), 76.18 g/m^2.7(ht)^ overall moderate decreased left ventricular systolic function (segmental); severe hypocontractility of basal anteroseptal, mid anteroseptal, apical septal, apical walls; mild hypocontractility of mid anterior, apical anterior walls; ejection fraction = 28 %^ normal left ventricular size; LVIDd = 4.6 cm Right Ventricle : mild to moderate [decreased right ventricular function RV: ABNORMAL FUNCTION] mild [right ventricular dilatation RV: ABNORMAL SIZE] right ventricle not well seen. Left Atrium : mild left atrial dilatation ; area-4ch = 21 cm2, length-4ch = 7 cm Right Atrium : normal inferior vena cava; size = 1.4 cm normal right atrial size; area 4-ch = 18 cm2 Aortic Valve : aortic sclerosis probable minimal aortic regurgitation no evidence for valvular aortic stenosis Mitral Valve : Abnormal Mitral Tissue Prosthesis: partially obstructed and high gradient; cannot exclude fibrocalcification, partial thrombosis or vegetation ; suggest TEE consistent with abnormal mitral prosthesis (tissue); pressure half-time = 180 millisec, mean MV gradient = 14 mmHg, peak gradient = 38 mmHg moderate mitral stenosis; pressure half-time = 180 millisec, area by Doppler = 1.32 cm2 [minimal mitral regurgitation MV: BORDERLINE REGURGITATION] Tricuspid Valve : moderate pulmonary hypertension; peak CW velocity = 3.7 m/sec, peak gradient = 55 mmHg, estimated RA pressure = 5 mmHg, RV sys. pressure = 60 mmHg mild to moderate tricuspid regurgitation Pulmonic Valve : mild pulmonic regurgitation Pericardium : no evidence for pericardial effusion Aorta : normal sinus of valsalva dimension; diameter = 3.6 cm Miscellaneous : study performed with patient supine

[ANONYMIZED] Definity® precision microbubble contrast used to enhance endocardial border definition ^ = number or calculation differs from reader's assessment [ANONYMIZED] Ht. : Wt. : BSA : 63.00 in 132.00 lbs 1.62 m2 HR : BP : 53 /min 138/67 mmHg (Before) 2-D Guided Measurement and Calculations Normal Ranges Linear Left Ventricle IV Septum-thickness Diastole (SWTd) 1.5 cm 0.8 -1.1 cm LV Posterior wall-thickness Diastole (PWTd) 1.4 cm 0.8 - 1.1 cm Dimensions (A. S. E.) Diastole (Dd) 4.6 cm Systole (Ds) 3.6 cm Calculated values Fractional shortening 22 % End-diastolic volume 97 63 mL 50 - 90 mL/m2 End-systolic volume 54 34 mL 30 - 70 mL/m2 Stroke volume 43 27 mL Ejection fraction 44 % 55 - 70 % ^ A. S. E. : Measurement technique according to American Society of Echocardiography Apical 2-D measurements and calculations of left ventricle 4-chamber 2-chamber Biplane End-diastolic volume 83 mL End-systolic volume 60 mL Stroke volume 23 mL Ejection fraction 28 % Page 4 of 4

FIGURE 7B

ANONYMIZED Indications: Hypertensive heart disease without heart failure. Dyspnea, unspecified Procedure: TTE - Rest Only D+C, Complete, w/o contrast 2D Measurements Left Atrium LAVi BP 64.6 ml/m² LA As 26.7 cm² LVIDd 3.3 cm (3.8-5.2) LA Vol BP 97.6 ml LVIDs 2.1 cm (2.2-3.5) RA Vol 37.1 ml (15-27) LV%fs 36.4 % RA Area 15.6 cm² LVEDV 43.7 ml (59-136) RAVi 24.5 ml/m² LVESV 15.2 ml IVSd 1.5 cm LV EF BP 74.5 % (54-74) LVPWd 1.3 cm (0.6-0.9) LVEDV BP 113.5 ml (46-106) Ao Rtd 3 cm LVESV BP 29 ml (14-42) LVOT 1.9 cm LV SV BP 84.5 ml IVS/LVPW 1.2 Doppler Measurements LVOT LVOTpkVel 1.3 m/s (0.7-1.1) LVOT VTI 32.3 cm LVOTpkPG 7.1 mmHg LVOT SV 74.7 ml AV Forward Flow AV VTI 59.8 cm AV pkPG 27.2 mmHg Area (VTI) 1.5 cm² (3-5) AV mnPG 14.4 mmHg Index 1 cm²/m² Area (Vel) 1.4 cm² (3-5) AV pkVel 2.6 m/s (1-1.7) AV mnVel 1.8 m/s MV Forward Flow MV pkVel 2 m/s MV DeTm 275.6 ms MV pkPG 15.9 mmHg MV pkE 1.8 m/s (0.6-1.3) MV mnVel 1 m/s MV pkA 0.9 m/s MV mnPG 4.6 mmHg MV E/A 2.1 MV VTI 48.5 cm MV DeSlp 6.7 m/s² TV Regurg Flow TR pkVel 3.4 m/s (0.3-0.7) TR pkPG 47.5 mmHg Left ventricle: Small left ventricular size. Mild to moderate left ventricular hypertrophy. Hyperdynamic left ventricular systolic function. The estimated left ventricular ejection fraction is >70%. No regional wall motion abnormalities are seen. Likely elevated LV filling pressure. Right ventricle: Normal right ventricular size RV: NORMAL SIZE . Normal right ventricular function RV: NORMAL FUNCTION . Left atrium: Severely dilated left atrium. Right atrium: Mildly dilated right atrial size. Mitral valve: Mitral annular calcification with calcification and restriction of posterior mitral valve leaflet. No mitral stenosis. Mild mitral regurgitation MV: BORDERLINE REGURGITATION . Aortic valve: Fibrocalcific trileaflet aortic valve with reduced systolic opening. Aortic valve area 1.4 cm2, with peak velocity 2.9 m/s and mean pressure gradient 17 mmHg, consistent with moderate aortic stenosis. DVI 0.50 Mild aortic regurgitation. Tricuspid valve: Structurally normal tricuspid valve without stenosis. Mild tricuspid regurgitation. As assessed from the tricuspid regurgitant jet, the pulmonary artery systolic pressure is 50 mm Hg, moderate pulmonary hypertension.

ANONYMIZED Pulmonic valve: The pulmonic valve is not well visualized. Pericardium: No pericardial effusion. Aortic root: Normal aortic root size. The aortic root is calcified. Miscellaneous: No previous study available for comparison. Conclusion Mild to moderate left ventricular hypertrophy. Small left ventricle with hyperdynamic left ventricular systolic function (>70%). Normal right ventricular size RV: NORMAL SIZE Normal right ventricular size and systolic function RV: NORMAL SIZE AND FUNCTION . Severely dilated left atrium. Mitral annular calcification without stenosis. Mild mitral regurgitation MV: BORDERLINE REGURGITATION . Moderate aortic stenosis. Mild aortic regurgitation. Mild tricuspid regurgitation. moderate pulmonary hypertension. Left pleural effusion is seen.

ANONYMIZED

FIGURE 7C

Race / Ethnicity

Age / Sex

External Validation  Internal Testing

Female  Male

Figure 24A:
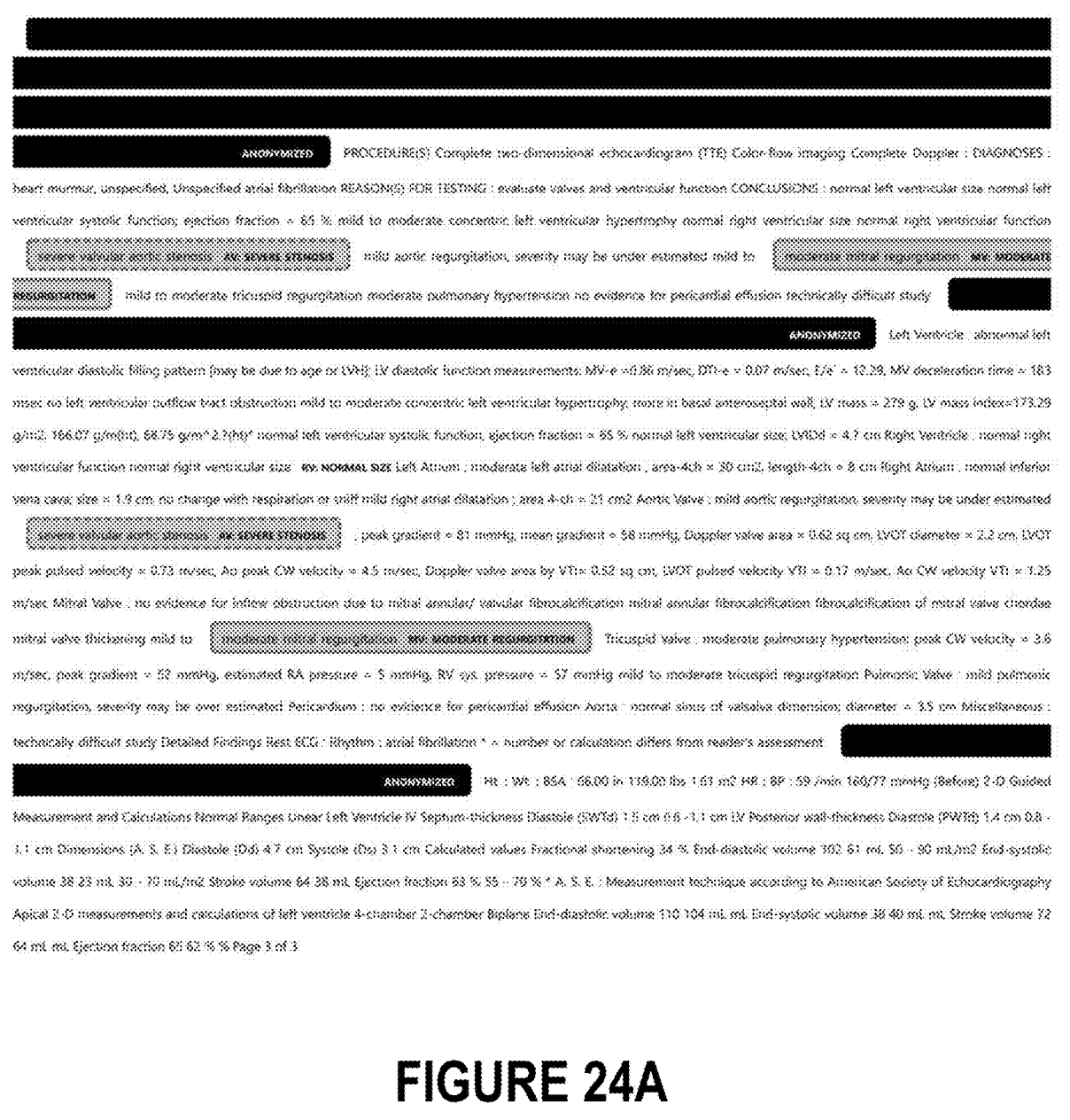

ANONYMIZED PROCEDURE(S) Complete two-dimensional echocardiogram (TTE) Color-flow imaging Complete Doppler : DIAGNOSES : heart murmur, unspecified, Unspecified atrial fibrillation REASON(S) FOR TESTING : evaluate valves and ventricular function CONCLUSIONS : normal left ventricular size normal left ventricular systolic function; ejection fraction = 85 %; mild to moderate concentric left ventricular hypertrophy normal right ventricular size normal right ventricular function SEVERE VALVULAR AORTIC STENOSIS AV SEVERE STENOSIS mild aortic regurgitation, severity may be under estimated mild to MODERATE MITRAL REGURGITATION MV MODERATE REGURGITATION mild to moderate tricuspid regurgitation moderate pulmonary hypertension no evidence for pericardial effusion technically difficult study ANONYMIZED Left Ventricle : abnormal left ventricular diastolic filling pattern (may be due to age or LVH); LV diastolic function measurements: MV-e =0.86 m/sec, DTI-e = 0.07 m/sec, E/e' = 12.29, MV deceleration time = 183 msec no left ventricular outflow tract obstruction mild to moderate concentric left ventricular hypertrophy, more in basal anteroseptal wall, LV mass = 279 g, LV mass index=173.29 g/m2, 166.07 g/m(ht), 68.76 g/m^2.7(ht)' normal left ventricular systolic function; ejection fraction = 85 % normal left ventricular size; LVIDd = 4.7 cm Right Ventricle : normal right ventricular function normal right ventricular size RV NORMAL SIZE Left Atrium : moderate left atrial dilatation , area-4ch = 30 cm2, length-4ch = 8 cm Right Atrium : normal inferior vena cava; size = 1.9 cm no change with respiration or sniff mild right atrial dilatation ; area 4-ch = 21 cm2 Aortic Valve : mild aortic regurgitation severity may be under estimated SEVERE VALVULAR AORTIC STENOSIS AV SEVERE STENOSIS , peak gradient = 81 mmHg, mean gradient = 58 mmHg, Doppler valve area = 0.62 sq cm, LVOT diameter = 2.2 cm, LVOT peak pulsed velocity = 0.73 m/sec, Ao peak CW velocity = 4.5 m/sec, Doppler valve area by VTI= 0.52 sq cm, LVOT pulsed velocity VTI = 0.17 m/sec, Ao CW velocity VTI = 1.25 m/sec Mitral Valve : no evidence for inflow obstruction due to mitral annular/ valvular fibrocalcification mitral annular fibrocalcification fibrocalcification of mitral valve chordae mitral valve thickening mild to MODERATE MITRAL REGURGITATION MV MODERATE REGURGITATION Tricuspid Valve : moderate pulmonary hypertension: peak CW velocity = 3.6 m/sec, peak gradient = 52 mmHg, estimated RA pressure = 5 mmHg, RV sys. pressure = 57 mmHg mild to moderate tricuspid regurgitation Pulmonic Valve : mild pulmonic regurgitation, severity may be over estimated Pericardium : no evidence for pericardial effusion Aorta : normal sinus of valsalva dimension; diameter = 3.5 cm Miscellaneous : technically difficult study Detailed Findings Rest ECG : Rhythm : atrial fibrillation * = number or calculation differs from reader's assessment ANONYMIZED ANONYMIZED Ht : Wt : 85A : 66.00 in 119.00 lbs 1.61 m2 HR : BP : 59 /min 160/77 mmHg (Before) 2-D Guided Measurement and Calculations Normal Ranges Linear Left Ventricle IV Septum-thickness Diastole (SWTd) 1.5 cm 0.6 -1.1 cm IV Posterior wall-thickness Diastole (PWTd) 1.4 cm 0.6 - 1.1 cm Dimensions (A. S. E.) Diastole (Dd) 4.7 cm Systole (Ds) 3.1 cm Calculated values fractional shortening 34 % End-diastolic volume 102 61 mL 56 - 90 mL/m2 End-systolic volume 38 23 mL 30 - 70 mL/m2 Stroke volume 64 38 mL Ejection fraction 63 % 55 - 70 % * A. S. E. : Measurement technique according to American Society of Echocardiography Apical 2-D measurements and calculations of left ventricle 4-chamber 2-chamber Biplane End-diastolic volume 110 104 mL mL End-systolic volume 38 40 mL mL Stroke volume 72 64 mL mL Ejection fraction 85 62 % % Page 3 of 3

SURFACING INSIGHTS INTO LEFT AND RIGHT VENTRICULAR DYSFUNCTION THROUGH DEEP LEARNING

CROSS-REFERENCE TO RELATED PATENT APPLICATIONS

This application is a continuation of U.S. Non-Provisional application Ser. No. 17/714,060, filed Apr. 5, 2022, which is incorporated by reference as if expressly set forth in its entirety herein.

TECHNICAL FIELD

Various embodiments pertain to approaches to quantifying left and right ventricular dysfunction and valvular disease in an automated manner.

BACKGROUND

Heart failure represents a significant health burden, with an estimated 6.2 million people affected in the United States and at least 64 million people affected worldwide. Considerable attention has been paid to the pathophysiology of left ventricular ("LV") failure. However, because of the anatomical and functional proximity of the ventricles, either LV failure or right ventricular ("RV") failure can precipitate biventricular involvement, with even subclinical RV dysfunction having been found to be associated with the risk of LV failure. Patients with biventricular failure tend to have significantly worse outcomes, with a two-year survival rate of roughly 23 percent as opposed to a two-year survival rate of roughly 71 percent in patients with isolated LV failure. Studies have also shown that RV dysfunction can be indicative of prognosis independent of LV dysfunction for several cardiovascular diseases. Early detection of heart failure creates the possibility of more efficient implementation of guideline-directed therapy and lifestyle modifications, which have been shown to improve overall outcomes for all forms of heart failure in addition to slowing the progression of cardiovascular diseases.

Left ventricular ejection fraction ("LVEF") is one of the most widespread hemodynamic parameters that is currently available in cardiovascular medicine. Among many possible uses, LVEF—as a measure of ventricular function—can be used to quantify progression of disease and response to treatment, as well as predict mortality independently. LVEF measurements are most readily obtained by transthoracic echocardiography, and therefore echocardiography is one of the procedures most commonly billed to private insurers, Medicare, and Medicaid in the United States. However, significant barriers remain to obtaining LVEF measurements in outpatient settings or resource-limited settings without a sufficient number of trained echocardiographers and logical support. Moreover, there remains significant interobserver and intraobserver variability in measuring LVEF. Furthermore, trajectories of LVEF over time may be more useful than isolated measurements, requiring repeated echocardiograms (and thus, visits to healthcare facilities—such as hospitals and clinics—for patients).

In contrast, RV failure has classically been within the realm of clinical diagnosis, with no specific biomarkers or agreed-upon guidelines for interpretation of electrocardiograms ("ECGs"). An ECG is a common test that is performed record the electrical signals in the heart, generally for the purpose of diagnosing or monitoring problems with the heart. Numerical measurements of RV function, such as right ventricular ejection fraction ("RVEF"), are not as readily available because of difficulties in measurement from conventional transthoracic echocardiography. Alternate methods to assess RV function, such as tricuspid annular systolic plane excursion, have demonstrated some promise in some settings but there remain challenges in common scenarios, such as measuring progression of a disease or assessing RV function following cardiac surgery. Three-dimensional echocardiography, strain imaging, and cardiac magnetic resonance ("CMR") are promising replacements but are impractical for use as screening modalities cause of concerns about cost and availability. Thus, assessment of the role of RV function in the pathophysiology of cardiovascular disease has, to date, been underappreciated.

For these reasons, there exists a pressing need for a readily available and inexpensive tool to measure, screen, or predict left and right ventricle function. The ECG is a cardinal investigation in the practice of cardiology. It is ubiquitous and inexpensive, and therefore is often the first investigation performed when a patient enters a healthcare setting with symptoms indicative of heart problems. However, the ECG has an upper bound of usefulness secondary to its skill requirement and subjectivity. Additionally, healthcare professions may not be able to identify subtle patterns that might indicate subclinical pathology, especially for conditions for which there are no interpretation guidelines. Simply put, the measurements generated during the ECG can be difficult to analyze even by healthcare professionals who have been trained to do so, and instances of cardiovascular disease may go undetected as a result.

Artificial intelligence—especially its subfield of deep learning ("DL")—offers the promise of automated analysis of physiological data to surface insights that might otherwise be unattainable through manual analyses. DL-based algorithms that rely on architectures such as convolutional neural networks ("CNNs") are fundamentally distinct from traditional machine learning approaches. DL-based algorithms are able to learn complex representations in order to recognize patterns more effectively and efficiently, unlike traditional machine learning approaches that rely heavily on manual input to design appropriate feature extractors.

Artificial intelligence has begun playing an increasing role in healthcare. One of the most promising applications of artificial intelligence is diagnostics. As an example, radiological investigations have historically required interpretation by a radiologist in order to obtain a diagnosis. Due to the increasing demands on radiologists—and the increasing costs of those radiologists—models have been developed in an attempt to automate aspects of the diagnostic workflow. These models can be applied to digital images in order to produce outputs (also called "predictions") that are intended to facilitate the diagnostic workflow.

Successfully incorporating artificial intelligence into routine clinical practice relies upon achieving accuracy and consistency that is not inferior to healthcare professionals. Other benefits—like cost, accessibility, and speed—must also be achieved. For these reasons, artificial intelligence has been incorporated into routine clinical practice in a methodical manner despite its potential.

Artificial intelligence has the potential to meaningfully transform how ailments are diagnosed. Simply put, evidence of ailments can be surfaced earlier through automated analysis of physiological data, potentially leading to improved outcomes. Despite its potential, artificial intelligence has not been widely adopted across diagnostic workflows. For example, many of the models developed to augment diagnostic workflows were designed and then trained to be applied to digital images to identify indications of cancer. However, artificial intelligence could also be employed to better understand other ailments.

BRIEF DESCRIPTION OF THE DRAWINGS

FIG. 3 includes a flow diagram of a process for training a neural network to detect right ventricular dysfunction through analysis of information related to left ventricular function.

FIG. 4 includes a flow diagram of another process for training a neural network to infer right heart status from an analysis of left ventricular ejection fraction ("LVEF").

FIG. 5 reflects the patient profile used to train and then test a model.

FIG. 6 illustrates the general workflow of obtaining and then processing the physiological data to be used for training and testing.

FIGS. 7A-C include examples of anonymized, annotated transthoracic echocardiogram reports that have been processed using rules that are implementable by a natural language processing algorithm.

FIG. 24A-C include examples of anonymized, annotated echo reports that have been processed using those rules developed for aortic stenosis.

Figure 1:
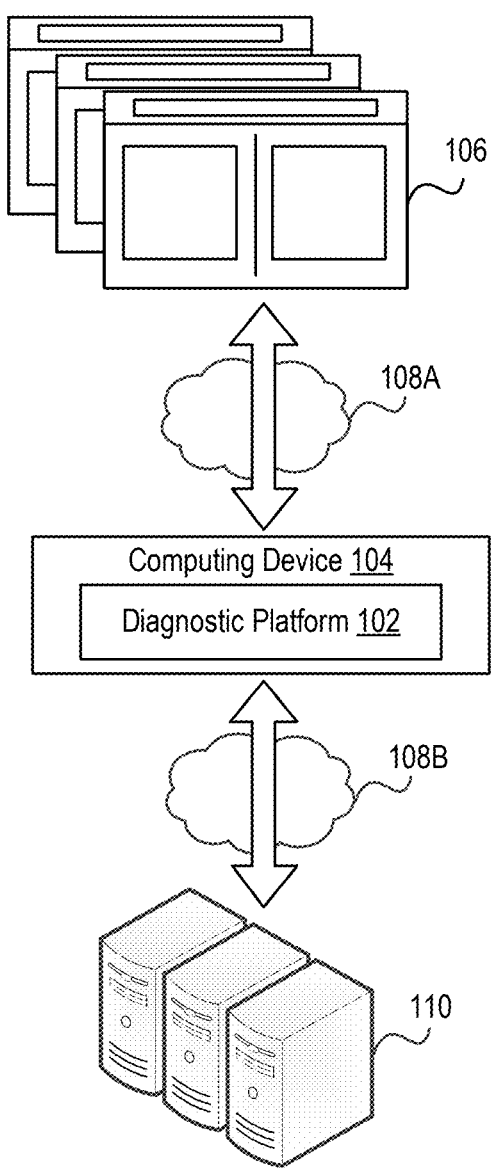
FIG. 1 illustrates a network environment that includes a diagnostic platform that is executed by a computing device.

Embodiments are illustrated by way of example and not limitation in the drawings. While the drawings depict various embodiments for the purpose of illustration, those skilled in the art will recognize that alternative embodiments may be employed without departing from the principles of the technology. Accordingly, while specific embodiments are shown in the drawings, the technology is amenable to various modifications

DETAILED DESCRIPTION

Recent breakthroughs in artificial intelligence have demonstrated that much more information may be available from the ECG to diagnose cardiovascular disease (and other diseases) than is currently leveraged. Deep learning ("DL")—which is a class of machine learning that uses hierarchical networks to extract lower-dimensional features from higher-dimensional data provided as input—has demonstrated significant potential for enabling ECG-based predictions that are helpful in rendering diagnoses. For example, DL has been used to identify patients with atrial fibrillation while in normal sinus rhythm, predict incident atrial fibrillation, identify patients who are amenable to cardiac resynchronization therapy, evaluate left ventricular diastolic function ("LVDF"), evaluate patients with echocardiographically concealed long QT syndrome ("LQTS"), predict the risk of sudden cardiac death, and predict instances of low LVEF.

Introduced here are approaches to developing, training, and implementing algorithms to cardiac dysfunction through automated analysis of physiological data. As an example, a model may be developed and then trained to quantify left and right ventricular dysfunction using ECG waveform data (or simply "ECG data") that is associated with a population of individuals who are diverse in terms of age, gender, ethnicity, socioeconomic status, and the like. Generally, ECG data available can be obtained in vector form and then converted into digital images that are shown to the model for training purposes. However, the ECG data could instead be presented to the model in vector form. This approach to training allows the model to predict the presence of left and right ventricular dysfunction in a diverse population. Also introduced here is a regression framework for predicting numeric values of LVEF.

For the purpose of illustration, these approaches may be described in the context of determining whether a given cardiovascular disease is present based on an analysis of predicted values for LVEF. However, these approaches may be similarly applicable to other cardiovascular diseases. Moreover, these approaches could be used to establish disease progression in addition to, or instead of, disease presence.

Moreover, embodiments may be described in the context of executable instructions for the purpose of illustration. However, those skilled in the art will recognize that aspects of the technology could be implemented via hardware, firmware, software, or any combination thereof. As an example, a computer program that is representative of a computer-aided diagnostic platform (also called a "CADx platform" or simply "diagnostic platform") designed to perform aspects of the approaches described herein may be executed by the processor of a computing device. As another example, aspects of the approaches described herein may be executed by an application-specific integrated circuit ("ASIC") that is customized to do so.

Terminology

Brief definitions of terms, abbreviations, and phrases used throughout the application are given below.

The terms "connected," "coupled," and variants thereof are intended to include any connection or coupling between two or more elements, either direct or indirect. The connection or coupling can be physical, logical, or a combination thereof. For example, objects may be electrically or communicatively connected to one another despite not sharing a physical connection.

The term "module" may refer broadly to hardware, firmware, software, or combinations thereof. Modules are typically functional components that generate one or more outputs based on one or more inputs. A computer program—like the diagnostic platform—may include modules that are responsible for completing different tasks, though those modules may work in concert with one another (e.g., the output produced by one module may be provided to another module as input).

Overview of Diagnostic Platform

FIG. 1 illustrates a network environment 100 that includes a diagnostic platform 102 that is executed by a computing device 104. An individual (also called a "user") may be able to interact with the diagnostic platform 102 via interfaces 106. For example, a user may be able to access an interface through which physiological data is processed in advance of being used to train a model. As another example, a user may be able to access an interface through which physiological data of interest can be identified and then outputs produced by a model to which the physiological data is applied can be reviewed.

As shown in FIG. 1, the diagnostic platform 102 may reside in a network environment 100. Thus, the computing device 104 on which the diagnostic platform 102 resides may be connected to one or more networks 108A-B. Depending on its nature, the computing device 104 could be connected to a personal area network (PAN), local area network (LAN), wide area network (WAN), metropolitan area network (MAN), or cellular network. For example, if the computing device 104 is a computer server, then the computing device 104 may be accessible to users via respective computing devices that are connected to the Internet via LANs.

The interfaces 106 may be accessible via a web browser, desktop application, mobile application, or another form of computer program. For example, to interact with the diagnostic platform 102, a user may initiate a web browser on the computing device 104 and then navigate to a web address associated with the diagnostic platform 102. As another example, a user may access, via a desktop application, interfaces that are generated by the diagnostic platform 102 through which she can select physiological data for analysis, review analyses of the physiological data, and the like. Accordingly, interfaces generated by the diagnostic platform 102 may be accessible to various computing devices, including mobile phones, tablet computers, desktop computers, and the like.

Generally, the diagnostic platform 102 is executed by a cloud computing service operated by, for example, Amazon Web Services®, Google Cloud Platform™, or Microsoft Azure®. Thus, the computing device 104 may be representative of a computer server that is part of a server system 110. Often, the server system 110 is comprised of multiple computer servers. These computer servers can include different types of data (e.g., information regarding patients, such as demographic information and health information), algorithms for processing, presenting, and analyzing the data, and other assets. Those skilled in the art will recognize that this data could also be distributed among the server system 110 and computing devices. For example, sensitive health information associated with a patient may be stored on, and initially processed by, a computing device that is associated with her healthcare provider, such that the sensitive health information is obfuscated before being transmitted to the server system 110 for further processing.

As mentioned above, aspects of the diagnostic platform 102 could be hosted locally, for example, in the form of a computer program executing on the computing device 104. Several different versions of computer programs may be available depending on the intended use. Assume, for example, that a user would like to actively guide the process by which physiological data to be analyzed is generated, retrieved, or otherwise obtained. In such a scenario, the computer program may allow for the selection of patients or physiological data, application of models, and analysis of outputs produced by those models. Alternatively, if the user is simply interested in reviewing analyses of outputs produced by models upon being applied to physiological data, the computer program may be "simpler."

Figure 2A:
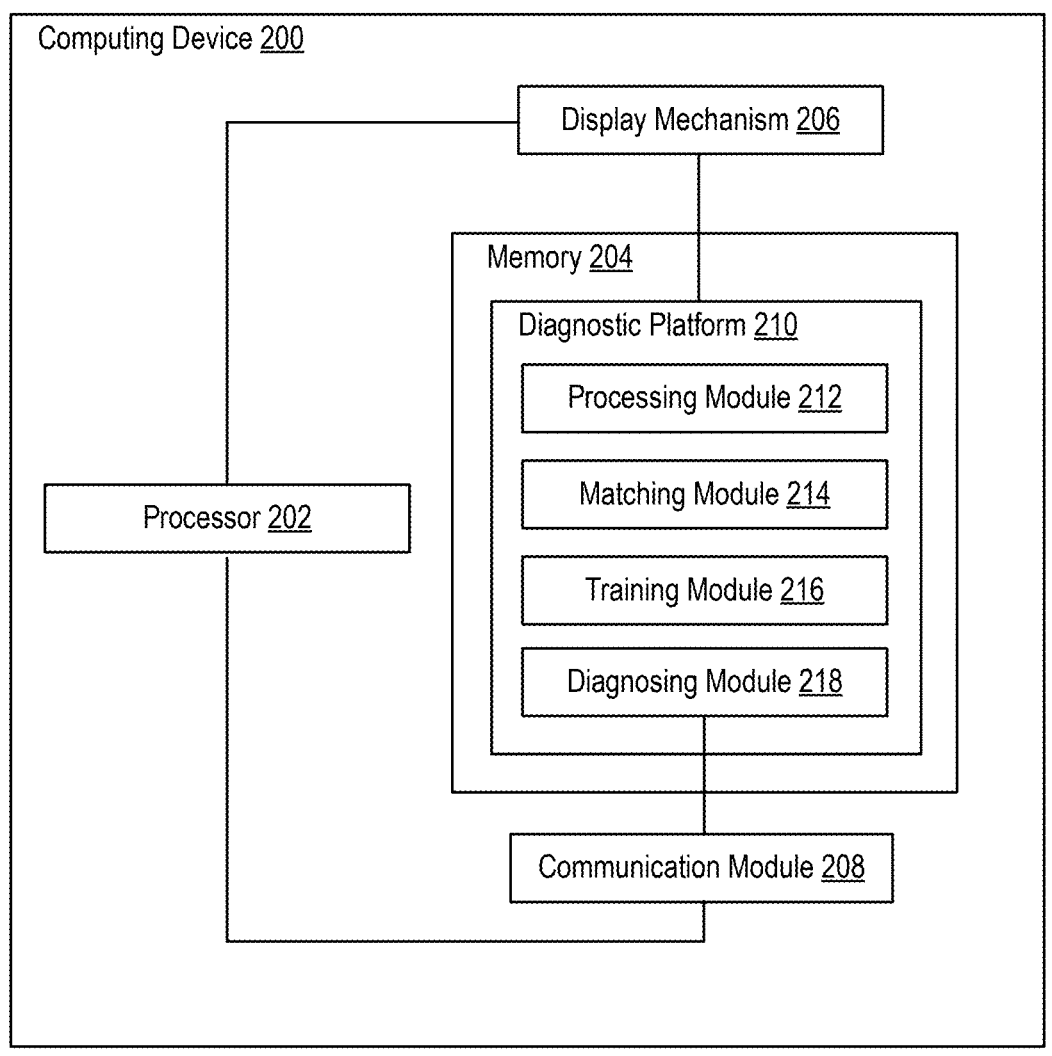
FIG. 2A illustrates an example of a computing device that is able to implement a diagnostic platform designed to assist in diagnosing patients with cardiac ailments.

FIG. 2A illustrates an example of a computing device 200 that is able to implement a diagnostic platform 210 designed to assist in diagnosing patients with cardiac ailments. As shown in FIG. 2A, the computing device 200 can include a processor 202, memory 204, display mechanism 206, and communication module 208. Each of these components is discussed in greater detail below. Those skilled in the art will recognize that different combinations of these components may be present depending on the nature of the computing device 200. For example, if the computing device 200 is a computer server that is part of a server system (e.g., server system 110 of FIG. 1), then the computing device 200 may not include the display mechanism 206.

The processor 202 can have generic characteristics similar to general-purpose processors, or the processor 202 may be an ASIC that provides control functions to the computing device 200. The processor 202 can be coupled to all components of the computing device 200, either directly or indirectly, for communication purposes.

The memory 204 may be comprised of any suitable type of storage medium, such as static random-access memory ("SRAM"), dynamic random-access memory ("DRAM"), electrically erasable programmable read-only memory ("EEPROM"), flash memory, or registers. In addition to storing instructions that can be executed by the processor 202, the memory 204 can also store data generated by the processor 202 (e.g., when executing the modules of the diagnostic platform 210). Note that the memory 204 is merely an abstract representation of a storage environment. The memory 204 could be comprised of actual integrated circuits (also called "chips").

The display mechanism 206 can be any mechanism that is operable to visually convey information to a user. For example, the display mechanism 206 may be a panel that includes light-emitting diodes ("LEDs"), organic LEDs, liquid crystal elements, or electrophoretic elements. In some embodiments, the display mechanism 206 is touch sensitive. Thus, the user may be able to provide input to the diagnostic platform 210 by interacting with the display mechanism 206. Alternatively, the user may be able to provide input to the diagnostic platform 210 through some other control mechanism.

The communication module 208 may be responsible for managing communications external to the computing device 200. The communication module 208 may be wireless communication circuitry that is able to establish wireless communication channels with other computing devices. Examples of wireless communication circuitry include 2.4 gigahertz (GHz) and 5 GHz chipsets compatible with Institute of Electrical and Electronics Engineers (IEEE) 802.11—also referred to as "Wi-Fi chipsets." Alternatively, the communication module 208 may be representative of a chipset configured for Bluetooth®, Near Field Communication (NFC), and the like. Some computing devices—like mobile phones, tablet computers, and the like—are able to wirelessly communicate via separate channels. Accordingly, the communication module 208 may be one of multiple communication modules implemented in the computing device 200.

The nature, number, and type of communication channels established by the computing device 200—and more specifically, the communication module 208—may depend on the sources from which data is acquired by the diagnostic platform 210. Assume, for example, that the diagnostic platform 210 resides on a computer server of a server system (e.g., server system 100 of FIG. 1). In such embodiments, the communication module 208 may communicate with databases from which to obtain data. As further discussed below, the data could be representative of the electronic health records with ECG data, transthoracic echocardiogram reports, and the like.

For convenience, the diagnostic platform 210 is referred to as a computer program that resides in the memory 204. However, the diagnostic platform 210 could be comprised of hardware or firmware in addition to, or instead of, software. In accordance with embodiments described herein, the diagnostic platform 210 may include a processing module 212, a matching module 214, a training module 216, and a diagnosing module 218. These modules can be an integral part of the diagnostic platform 210. Alternatively, these modules can be logically separate from the diagnostic platform 210 but operate "alongside" it. Together, these modules may enable the diagnostic platform 210 to train models to detect right ventricular dysfunction through analysis of information related to left ventricular dysfunction. Said another way, the models may be able to simultaneously surface insights into left and right ventricular dysfunction for diagnostic purposes.

Figure 2B:
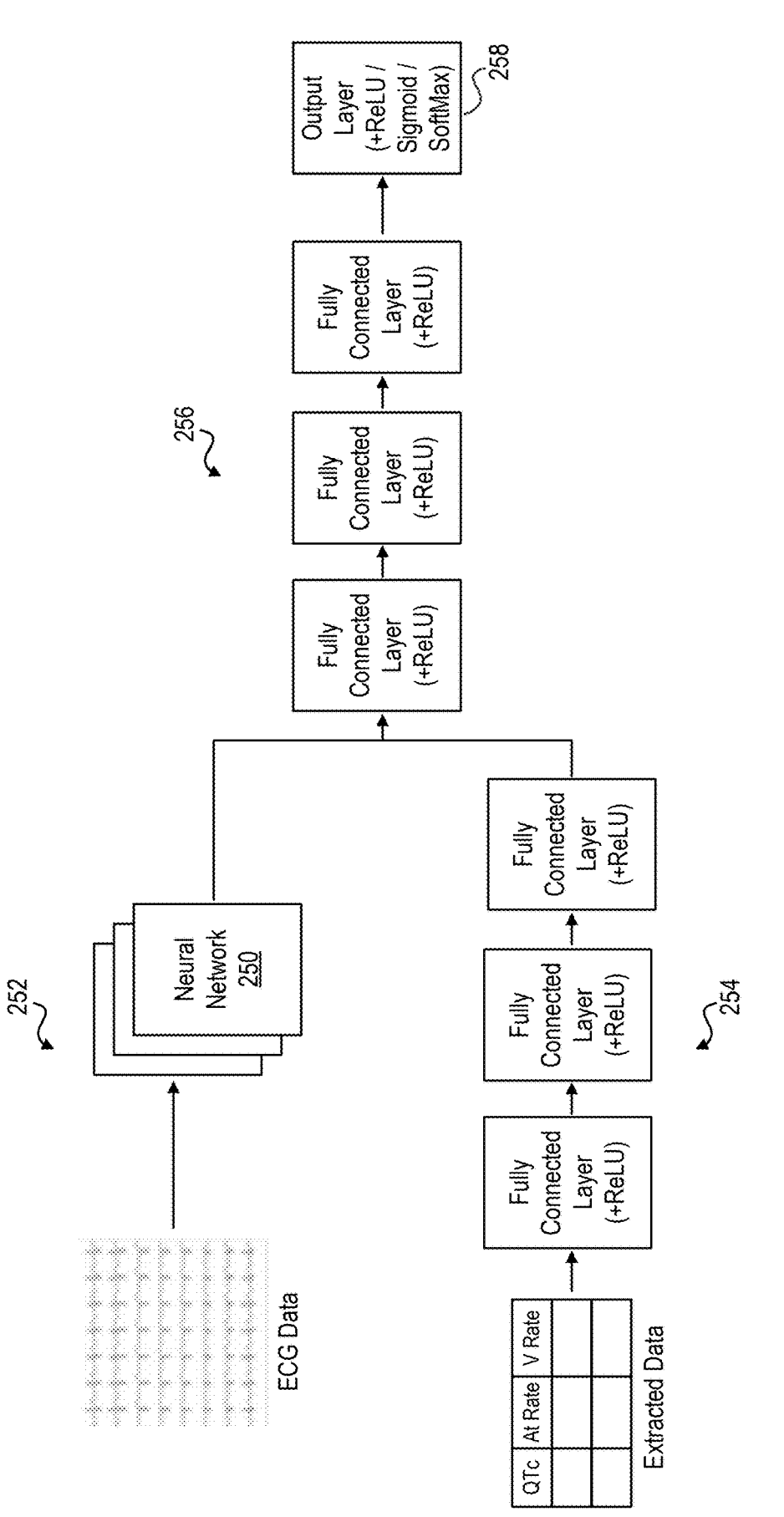
FIG. 2B illustrates an example architecture of a neural network that can be employed by the diagnostic platform of FIG. 2A.

As further discussed below, the model may be in the form of a neural network. FIG. 2B illustrates an example architecture of a neural network 250 that can be employed by the diagnostic platform 210 of FIG. 2A. As shown in FIG. 2B, extracted data (e.g., in tabular form) can be input into the fully connected layers in Branch A 252, while ECG data (e.g., in image form) can be input into the neural network 250 in Branch B 254. Intermediate layers 256 can create a composite input from the extracted data and neural network 250 for the final output layer 258. The activations and shape of the output layer 258 may depend on the output. Note that in FIG. 2B, "ReLU" stands for rectified linear unit. Those skilled in the art will recognize that the example architecture is provided for the purpose of illustration. Other architectures (e.g., with more layers, with fewer layers, with additional processing operations) could be employed by the diagnostic platform 210.

The processing module 212 may be responsible for applying operations to data that is acquired by the diagnostic platform 210. Assume, for example, that the diagnostic platform 210 receives input indicative of a selection of (i) a first database from which to obtain information that is generated as part of transthoracic echocardiograms ("TTEs") involving a first plurality of patients and (ii) a second database from which to obtain information that is generated as part of electrocardiograms involving a second plurality of patients. The processing module 212 may process (e.g., filter, reorder, or otherwise alter) the data acquired from the first and second databases so that it is usable by the other modules of the diagnostic platform 210.

Note that in some embodiments the first and second databases are associated with the same healthcare facility, while in other embodiments the first and second databases are associated with different healthcare facilities. Thus, the first database may be associated with a first healthcare facility, and the second database may be associated with a second healthcare facility. Moreover, the first database could be one of multiple databases from which to obtain information related to TTEs. Similarly, the second database could be one of multiple databases from which to obtain information related to electrocardiograms.

The operations performed by the processing module 212 can vary depending on the nature of the data.

From the first database, the processing module 212 may acquire electronic health records that are associated with a first plurality of patients. Each electronic health record may specify cardiac metrics such as the LVEF, or each electronic health record may include data from which the cardiac metrics can be computed, inferred, or otherwise derived. As an example, ECG data may be stored in the electronic health record in its raw form. In the event that values for LVEF are not readily extractable from the electronic health records, the processing module 212 may compute those values.

Generally, electronic health records do not include discrete metrics related to right ventricular dysfunction. As such, information regarding right ventricular dysfunction may need to be acquired from another source. From the second database, the processing module 212 may acquire transthoracic echocardiography ("echo") reports that are associated with a second plurality of patients. At a high level, an echo report is representative of a digital file that includes unstructured text related to determinations made by a healthcare professional during a TTE. To establish whether a given patient is experiencing right heart dysfunction, the processing module 212 may parse the unstructured text of the corresponding echo report in a semi- or fully-automated manner. For example, the processing module 212 may apply a natural language processing ("NLP") algorithm to the unstructured text of the corresponding echo report, so as to identify indicators of right heart dysfunction. The processing module 212 can assign or append a label to each echo report based on the indicators identified by the NLP algorithm.

The matching module 214 may be responsible for matching the electronic health records with the echo reports for training purposes. To train a model to diagnose instances of right ventricular dysfunction through analysis of information related to left ventricular function, associations must be learned by the model. To accomplish this, the matching module 214 can identify transthoracic echocardiogram-electrocardiogram pairs (also called "TTE-ECG pairs") by matching the electronic health records with the echo reports (and corresponding labels). Specifically, the matching module 214 may pair the echo reports with the electronic health records, such that each echo report is paired with electronic health records, if any, that include ECG data generated within a predetermined amount of time of that echo report. Matching of echo reports with electronic health records may be restricted to the training process, however. Once deployed, models may not require matching except by way of a post hoc analysis of confirmation of accuracy. During the training process, matching can be done for ECG data and echo reports on a per-patient basis over a specific temporal interval before and after each echo report. For example, for each echo report, matches may be sought several days (e.g., 3, 5, or 7 days) before and after that echo report. This may be done with the assumption that right ventricular parameters (and thus, cardiac health) will be largely stable over that temporal interval, and therefore can be used as labels for the model. Generally, the right ventricular parameters can be extracted from echo reports using NLP as further discussed below.

Thereafter, the training module 216 can provide the TTE-ECG pairs to a model as training data, so as to produce a trained model that is able to detect instances of right ventricular dysfunction through analysis of information related to left ventricular function. As an example, the trained model may be able to determine the likelihood that a patient is experiencing right ventricular systolic dysfunction ("RVSD") or right ventricular dilation ("RVD") based on a corresponding LVEF value.

In some embodiments, the model is a binary classification model that is trained to output predictions as to whether patients are experiencing right ventricular dysfunction. In such a scenario, the binary classification model may simply output a value of either one or zero to indicate whether there is evidence of right ventricular dysfunction. Rather than serve as a treating tool, the binary classification model may instead serve as a screening tool for establishing whether further examination—namely, by a healthcare professional—is necessary.

In other embodiments, the model is a multiclass classification model that is trained to output more detailed predictions. In contrast to the aforementioned binary classification model, the multiclass classification model may be trained to distinguish between different states or severities of right ventricular dysfunction. Thus, the multiclass classification model may learn to distinguish between mild, moderate, and severe right ventricular dysfunction. Additionally or alternatively, the multiclass classification model may learn to distinguish between different forms of right ventricular dysfunction. As an example, with sufficient training data, the multiclass classification model may learn to distinguish between indicators of RVSD and indicators of RVD. While the multiclass classification model could serve as a screening tool like the binary classification model, it could also serve as a treating tool. The predictions output by the multiclass classification tool could be used to identify appropriate "next steps." Those "next steps" could involve enrolling in a treatment program, scheduling examination by appropriate healthcare professional, etc.

Thereafter, the diagnostic platform 210 may receive input indicative of a request to use the trained model. As an example, the diagnostic platform 210 may receive input indicative of a selection of a patient for whom ECG data is available (e.g., from the electronic health record). Alternatively, the diagnostic platform 210 may receive input indicative of a selection of the ECG data itself. In response to receiving the input, the diagnosing module 218 can apply the trained model to the ECG data, so as to produce an output. As mentioned above, the nature of the output may depend on the nature of the trained model (e.g., whether the trained model is a binary or multiclass classification model). The output or analyses of the output can be posted to an interface for review. The interface may be viewable using the display mechanism 206 of the computing device, or the interface may be viewable on another computing device—in which case the output or analyses of the output may be transmitted to the other computing device using the communication module 208.

Other modules could also be included as part of the diagnostic platform 210. For example, a graphical user interface ("GUI") module may be responsible for generating the interface through which users can interact with the diagnostic platform 210, view outputs produced by the trained model, etc. As an example, a visualization component (or simply "visualization") that includes a visual depiction of the ECG data to which the trained model has been applied may be posted to an interface generated by the GUI module for consideration by a user. The visualization may be intended to illustrate how the trained model arrived at its prediction by identifying (e.g., using highlights, bounding boxes, etc.) features that were determined to be diagnostically relevant.

Methodologies for Predicting Diagnoses Through Analysis of Physiological Data FIG. 3 includes a flow diagram of a process 300 for training a neural network to detect right ventricular dysfunction through analysis of information related to left ventricular function. Note that while the process 300 is described in the context of a neural network, the process 300 may be similarly applicable to models having other architectures.

Initially, a diagnostic platform can receive input indicative of a selection of (i) a first dataset that is representative of information generated as part of a plurality of TTEs involving a first plurality of patients and (ii) a second dataset that is representative of information generated as part of a plurality of ECGs involving a second plurality of patients (step 301). For example, a user may select the first and second datasets through an interface generated by the diagnostic platform. As another example, a user may select healthcare facilities that are associated with the first and second datasets through an interface generated by the diagnostic platform. For instance, the user may specify one or more healthcare facilities from which to acquire, directly or indirectly, the first dataset, and the user may specify one or more healthcare facilities from which to acquire, directly or indirectly, the second dataset.

For each TTE, the first dataset can include unstructured text that provide insights into right ventricular function. The unstructured text may be representative of the notes taken a healthcare professional during or after each TTE.

For each ECG, the second dataset can include (i) an identifier that is associated with a corresponding patient, (ii) temporal information regarding a corresponding procedure, or (iii) a value for LVEF. Values for other cardiac metrics—and the raw data generated by each lead—may also be included in the second dataset. The second dataset may be representative of information that is derived from electronic health records of the second plurality of patients, or the second dataset may be representative the electronic health records themselves as discussed above.

The diagnostic platform can then establish outcomes of the TTEs based on an analysis of the first dataset (step 302). As mentioned above, the first dataset can include unstructured text that is related to right ventricle function. The diagnostic platform can gain insight into right ventricle function by examining the unstructured text. Assume, for example, that the diagnostic platform acquires a plurality of digital files that contain unstructured text related to the plurality of TTEs. Then, the diagnostic platform may execute an NLP algorithm such that a series of rules are applied to each digital file of the plurality of digital file, so as to establish the outcomes of each TTE of the plurality of TTEs. At a high level, each rule defines a linguistic criterion for establishing a likelihood that a given outcome occurred. As further discussed below, these linguistic criteria may define combinations and sequences of words that are indicative of cardiac health, specifically for the right ventricle. Note that more than one rule may correspond to a given outcome. As an example, multiple rules may be defined for establishing that functionality of the right ventricle is abnormal.

In some embodiments, the diagnostic platform filters the second dataset to ensure that outliers do not influence learning by the neural network. As an example, the diagnostic platform may filter the second dataset by discarding (i) data that is related to ECGs for which the LVEF value is above a first threshold and (ii) data that is related to ECGs for which the LVEF value is below a second threshold. The first and second thresholds could be static, or the first and second thresholds could be dynamic. For example, the diagnostic platform may discard outliers with >99, >95, or >90 percent LVEF in the population represented by the second dataset. Additionally or alternatively, the diagnostic platform may discard outliers with <1, <5, or <10 percent LVEF in the population represented by the second dataset.

Thereafter, the diagnostic platform can identify TTE-ECG pairs by pairing the plurality of TTEs with the plurality of ECGs, such that each TTE is paired with ECGs, if any, that occurred within a predetermined amount of time (step 303). As an example, the diagnostic platform may pair each TTE with ECGs performed within ±7 days, 10 days, 15 days, etc. The time at which each TTE was performed may be readily determinable from the first dataset, while the time at which each ECG was performed may be readily determinable from the second dataset.

The diagnostic platform can provide the TTE-ECG pairs and corresponding outcomes to the neural network as training data, so as to produce a trained neural network that is able to stratify patients (step 304). As part of its training, the neural network learns how the corresponding outcomes—which concern right ventricle function—relate to the left ventricle function indicated by LVEF values. The diagnostic platform can then store the trained neural network in a data structure (step 305). Often, the diagnostic platform appends information to the data structure, for example, in the form of metadata, that provides context for the first dataset, second dataset, first plurality of patients, second plurality of patients, outcomes, and the like. For example, the metadata may specify how many patients were included in the population used for training, as well as the demographic breakdown of the population used for training. As another example, the metadata may specify whether the neural network is designed and then trained to stratify patients among two categories (e.g., disease and no disease) or more than two categories (e.g., severe disease, moderate disease, mild disease, and no disease).

FIG. 4 includes a flow diagram of another process 400 for training a neural network to infer right heart status from an analysis of LVEF. Initially, a diagnostic platform can determine LVEF values for a first plurality of patients (step 401). For example, the diagnostic platform may acquire electronic health records associated with the first plurality of patients and then examine the electronic health records to determine a separate LVEF value for each patient of the first plurality of patients. Additionally, the diagnostic platform could filter the LVEF values by discarding (i) LVEF values that are above a first threshold or (ii) LVEF values that are below a second threshold. Additionally or alternatively, the diagnostic platform could remove variable consecutive LVEF values that are determined to correspond to a single patient. To accomplish this, the diagnostic platform can identify patients, if any, that are associated with more than one LVEF value and then, for each identified patient, discard the corresponding values in response to a determination that the difference between a lowest value and a highest value is greater than a predetermined amount.

Moreover, the diagnostic platform can acquire echo reports that are associated with a second plurality of patients (step 402). Generally, more ECG data is available than echo reports, and therefore the first plurality of patients may be larger in number than the second plurality of patients. Each echo report may include unstructured text that summarizes right heart status of a corresponding patient of the second plurality of patients. Then, the diagnostic platform can apply an NLP algorithm to the echo reports, so as to identify words that are indicative of right heart status (step 403). When executed, the NLP algorithm can implement rules that are designed to surface indicators of right heart status. Said another way, the NLP algorithm can identify words that are indicative of right heart functionality. The term "right heart health state" may be used to generally refer to the status or functionality of the right heart—namely, the right ventricle and right atrium. The diagnostic platform can then associate each echo report with a label that specifies the right heart status as determined for the corresponding patient of the second plurality of patients based on the words identified by the NLP algorithm (step 404). In embodiments where the neural network to be trained is representative of a binary classification model, the labels may simply indicate whether the echo reports correspond to instances of "disease" or "no disease." In embodiments where the neural network to be trained is representative of a multiclass classification model, the labels may provide more information. For example, the labels may indicate whether the echo reports correspond to instances of "severe disease," "moderate disease," "mild disease," or "no disease."

Thereafter, the diagnostic platform can match the echo reports with the electronic health records in a temporal manner to produce matched data (step 405). Step 405 of FIG. 4 may be similar to step 303 of FIG. 3. Additional information on how matches can be determined between echo reports and ECG data can be found below. The diagnostic platform can then provide the matched data to a neural network as training data, so as to produce a trained neural network that is able to infer right heart status from an analysis of LVEF values (step 406). Further, the trained neural network may be able to stratify patients among different severities of a right ventricular ailment based on the inferred right heart status. Examples of right ventricular ailments include RVSD and RVD.

Illustrative Application of Methodologies

A. Identifying Right and Left Ventricular Dysfunction From ECG Data

Figure 5:
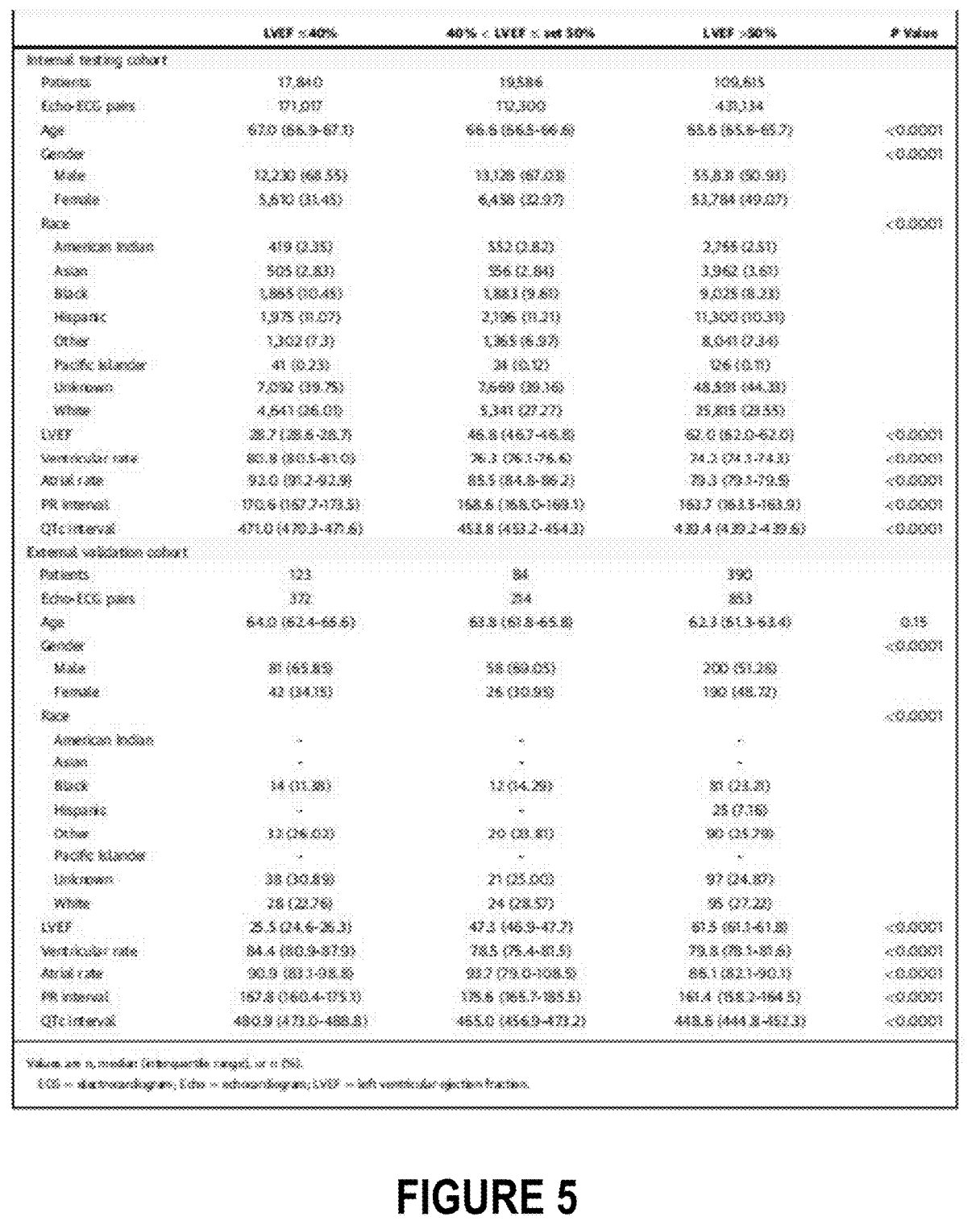

For the purpose of illustration, the approaches described herein have been used to analyze physiological data associated with patients corresponding to five different hospitals over a roughly 15-year period. These hospitals are located in the same geographical area—namely, the boroughs of New York City—but server a diverse population of patients. FIG. 5 reflects the patient profile used for training and testing purposes. Meanwhile, FIG. 6 illustrates the general workflow of obtaining and then processing the physiological data. In FIG. 6, the sources of data are indicated using solid lines while the processing steps are indicated using dashed lines. The numbers—which are provided solely for illustration—indicate datapoints that are retained for analysis following conditional filtering.

As shown in FIG. 6, the diagnostic platform can initially extract LVEF from the electronic health records ("EHRs") of the patients. The EHRs may be retrieved directly from the record systems of the hospitals, or the EHRs could be otherwise accessible (e.g., maintained by a third party). Specifically, LVEF values are abstracted from echo reports that are written or managed by healthcare professionals. Generally, each extracted record includes a unique identifier for the corresponding patient, the date and time of the echo, and the value of the LVEF as an integer. The diagnostic platform may be designed, programmed, or trained to identify LVEF values for more efficient extraction. Using this approach, the diagnostic platform acquired 444,786 reports for 219,437 patients.

For the reasons discussed above, details of RVSD or RVD may not be present within EHRs as discrete parameters. In scenarios where values for these metrics are not readily available, the diagnostic platform may acquire digital files that contain unstructured text related to echo reports. Here, for example, the diagnostic platform collects digital files in the Portable Document Format ("PDF") file format that contain unstructured text corresponding to 404,502 echo reports for 225,826 patients. As before, each collected record may contain a unique identifier for the corresponding patient and the date and time of the echo.

Meanwhile, the diagnostic platform obtained ECG data in the form of extensible Markup Language ("XML") files. Like the echo reports, the ECG data could be obtained from the record systems of the hospitals. Alternatively, the ECG data could be obtained from another source, for example, a system to which ECG data is uploaded following collection that is maintained by a manufacturer of the machinery that generates the ECG data. Each XML file can include demographic information for the corresponding patient, details about the testing location (e.g., the healthcare facility where the ECG was performed), per-lead parameters for the ECG, ECG diagnoses, and raw waveform data. Additional details regarding the ECG data can be found below.

For each outcome that is defined by an echo report, the diagnostic platform can pair the echo report with any ECG performed within a predetermined interval of time. Here, for example, the diagnostic platform pairs the echo report with any ECG performed within a time period of seven days before to seven days after the date of the echo. In this experiment, the diagnostic platform extracted 715,890 paired ECGs for 147,636 patients for prediction of LVEF and 761,510 paired ECGs for 148,227 patients for prediction of RV status. There was an overlap of 390,921 paired ECGs for 87,514 patients over the two datasets.

In reviewing the two datasets, there were several objectives.

First, the diagnostic platform elected to model LVEF in a classification framework, such that patients could be programmatically stratified for diagnostic purposes. LVEF was stratified into three clinically relevant ranges of (i) LVEF≤40 percent, (ii) LVEF>40 percent and ≤50 percent, and (iii) LVEF>50 percent. As none of these intervals overlap, the overall task can be considered a multiclass classification program. For comparison purposes, the diagnostic platform also assessed performance at classification of LVEF≤35 percent.

Second, the diagnostic platform attempted to model LVEF using a regression framework (i.e., directly predicting integer values of LVEF). For this problem, the target label was the LVEF value associated with each echo-ECG pair, and therefore no additional processing was required.

Right heart status was considered as a composite phenotype positive for either RVSD or RVD, as elicited from an echo report. The process for defining right heart status relied on use of NLP of the text from the echo reports, as further discussed below. Examples of phrases that could be used to define RVSD and RVD are listed in Table I. Echo-ECG pairs were labeled positive for the outcome and assigned a value of one in the event that either RVSD or RVD were determined to be present in any severity and a value of zero if RVSD and RVD were determined to be absent. As there are only two possible values for the outcome, the task may be considered a binary classification problem.

TABLE I

| Examples of phrases that could be used to discover instances of RVSD and RVD. | |
| --- | --- |
| Rule | Example Positive |
| RV Normal Size | |
| normal right {ventricle \| ventricular} {*} size | normal right ventricular size |
| right {ventricle \| ventricular} {*} normal {*} {LEMMA:size} | right ventricle is normal sized |
| rv size {*} normal | rv size is normal |
| right ventricle {*}{*}{*}{*} of normal {*} | right ventricle appears to be of normal size |
| RV Normal Function | |
| normal right {ventricle \| ventricular} function | normal right ventricular function |
| right {ventricle \| ventricular} wall motion {*} normal | right ventricular wall motion is normal |
| normal right ventricular wall motion | normal right ventricular wall motion |
| Right ventricular function {*} normal | right ventricular function is normal |

TABLE I-continued

| Examples of phrases that could be used to discover instances of RVSD and RVD. | |
| --- | --- |
| Rule | Example Positive |
| RV Size and Function Normal | |
| normal right {ventricle \| ventricular} size {STOP_WORD} {*} function | normal right ventricular size and systolic function |
| right ventricle {*}{*}{*}{*} normal {*} size {STOP_WORD} function | right ventricle is observed to have normal size and function |
| RV Abnormal Size | |
| dilated right ventricle | dilated right ventricle |
| right ventricular {dilation \| dilatation} | right ventricular dilation |
| rv size {*}{*} dilated | rv size is moderately dilated |
| Right ventricle {STOP_WORD} {NEGATE:not} dilated | right ventricle is very mildly dilated |
| RV Abnormal Function | |
| normal right {ventricle \| ventricular} size {STOP_WORD} (LEMMA:reduce} | normal right ventricular size and reduced function |
| right {ventricle \| ventricular} {*} {LEMMA:reduce} systolic function | right ventricle has reduced systolic function |
| {decreased \| reduced} right {ventricle \| ventricular} {*} function | Decreased right ventricular systolic function |
| right {ventricle \| ventricular} {*} function {*} {mildly \| moderately \| severely} | right ventricular function is moderately reduced |
| right ventricle {*} {hypokinetic \| akinetic} | right ventricle is hypokinetic |

To ensure the quality of the ECG data, the diagnostic platform may perform different processing and filtering operations. For example, the diagnostic platform may discard outliers with >90 percent LVEF (99.77th percentile) and <10 percent LVEF (0.18th percentile) within the patient population. Additionally, the value of LVEF generated from echo may be subject to inter-rater or inter-test variability. As the diagnostic platform considers data collected over an interval of time (e.g., ±7 days), if the difference in reported LVEF for a patient between two consecutive reports within the interval of time was greater than a threshold (e.g., >10 percent), both of the echo reports may be discarded.

As mentioned above, NLP may be employed by the diagnostic platform to extract outcomes from echo reports. To accomplish this, a rule-based approach may be implemented such that outcomes of interest can be extracted from the text contained within echo reports. Examples of outcomes of interest include RVSD, RVD, and mitral regurgitation ("MR"). An overall list of rules can be created and then iteratively expanded to ensure capture of the variability surrounding phrases detailing the same semantic concept. In some embodiments, the rules are manually defined by a user of the diagnostic platform. In other embodiments, rules are defined via a process that is partially or entirely automated. For example, upon receiving input indicative of a rule created by a user, the diagnostic platform may generate additional rules that are intended to cover comparable phrases. However, these additional rules may be rejectable by the user. Table I includes examples of rules for surfacing phrases indicative of health states of interest, while FIGS. 7A-C include examples of anonymized, annotated echo reports that have been processed using those rules.

Although RVSD and RVD were only considered in terms of presence or absence, additional rules could be created and then implemented to extract qualifiers of disease severity. In this experiment, a total of eight rules were created to be able to classify MR into normal, borderline (trace, minimal, mild), moderate, and severe disease.

Waveform data within XML files is normally formatted as one-dimensional collections (also called "vectors") of integers samples at a rate of 500 hertz ("Hz"), for example. Each vector may correspond to a lead, with each XML file containing data for leads I, II, and $V_1$-$V_6$. The length of these vectors can vary. For example, these vectors can extend to five seconds (2,500 samples) or ten seconds (5,000 samples) of recorded information for each lead in addition to longer rhythm strip recordings. To avoid potential artifacts causes by extending 2,500 samples to 5,000 samples, the diagnostic platform may restrict each sample to only the first five seconds of its recording. Furthermore, the ECG data may not include—or the diagnostic platform may simply not consider—data for leads III, aVF, aVL, or aVR. These leads may be considered to have no additional information as the data can be derived from linear transformations of the vectors representing the other leads. As such, these leads may not be included in the model developed by the diagnostic platform.

Figure 8:
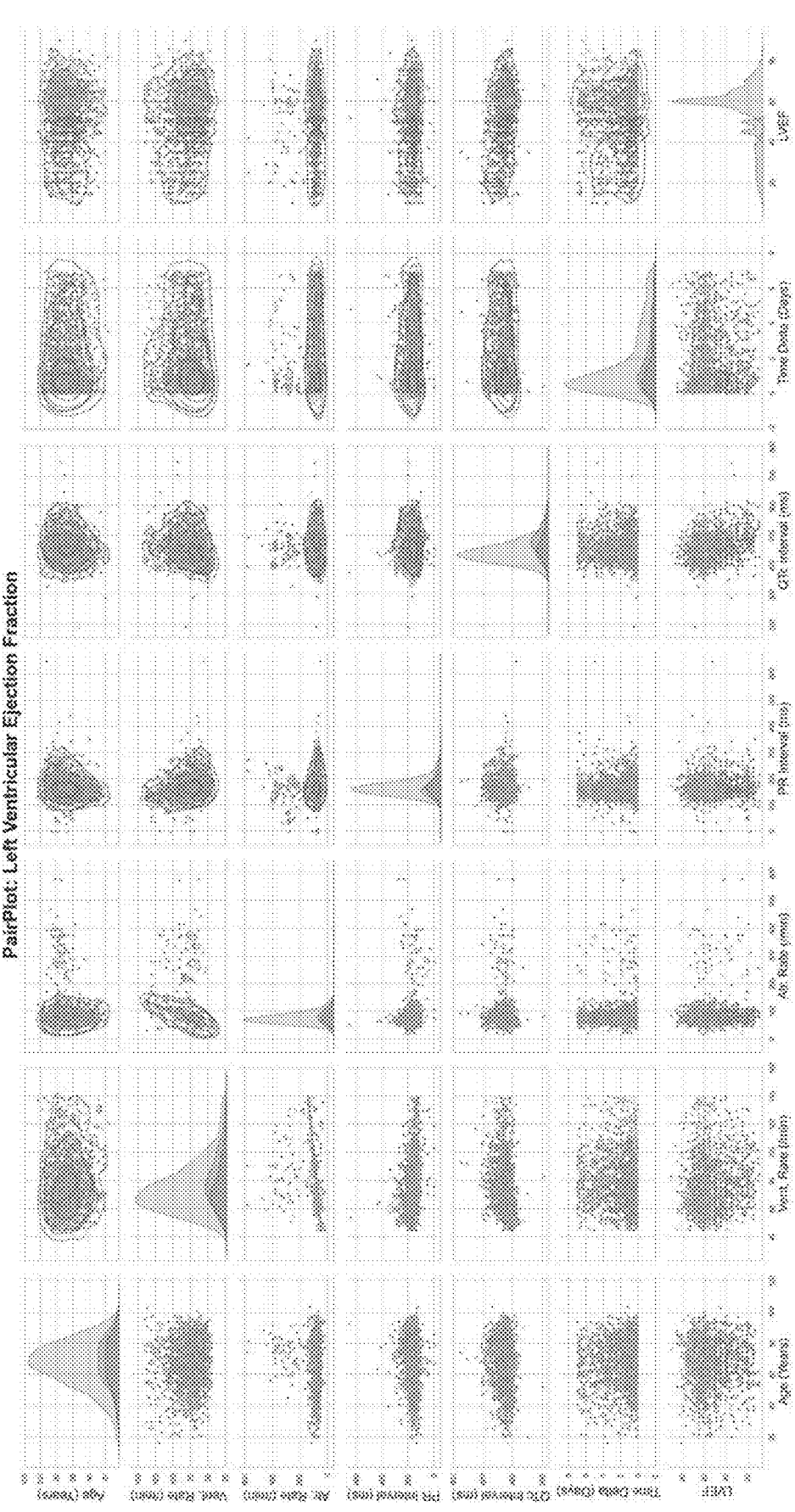
FIG. 8 includes a pair plot showing distribution of LVEF across different variables.
Figure 9:
FIG. 9 includes a pair plot showing distribution of right ventricular systolic dysfunction across different variables.

Patient age and cart-extracted parameters—such as corrected QT interval, PR interval, atrial rate, and ventricular rate—can also be acquired from XML files and used for input to the model. Overall distribution of input variables with respect to each outcome can be observed in the pair plots shown in FIGS. 8-9. These pair plots are representative of population level differences in variables associated with the model. Through testing, it has been found that input variables are not correlated with respect to each other or the outcome. Finally, no ECGs were excluded based on associated diagnoses, in the hope for generalizability across different pathologies.

ECG data comprised of arrays of numbers (e.g., in vector form) can be processed using either a one-dimensional convolutional neural network ("CNN") or a two-dimensional CNN. Typically, two-dimensional CNNs are more rigorous and computationally intensive, and therefore well suited to tasks like image processing and genomics studies. In this example, a two-dimensional CNN was selected because all healthcare entities may not store ECG data as vectors, as well as to be able to leverage pretrained, robust two-dimensional CNN architectures via transfer learning. Several different two-dimensional CNN architectures were assessed, and EfficientNet—a CNN architecture that uniformly scales all dimensions of depth, width, and resolution using a compound coefficient—was found to offer the best performance. Other CNN architectures could be used, however.

ECG data was initially collected from a series of healthcare facilities to form a dataset for internal testing. ECG data was also obtained from another healthcare facility to form a dataset of external validating. Through analysis of these ECG data, the diagnostic platform confirmed that no patients within the external validation dataset were included in the internal testing dataset. The relative distributions of the datasets across internal testing and external validating are shown in Tables II and III, respectively.

TABLE II

| | Population metrics of study population by RVSD and RVD, where values are mean or median (interquartile range). | | |
| --- | --- | --- | --- |
| | RVSD or RVD | Normal | P Value |
| | Internal Testing Cohort | | |
| Patients | 30,780 | 104,436 | |
| Echo-ECG Pairs | 278,877 | 425,815 | |
| Age | 65.8 (65.8-65.9) | 66.7 (66.7-66.8) | <0.0001 |
| Gender | | | <0.0001 |
| Male | 18,533 (60.21) | 51,122 (48.95) | |
| Female | 12,247 (39.79) | 53,314 (51.05) | |
| Race | | | <0.0001 |
| American Indian | 384 (1.25) | 962 (0.92) | |
| Asian | 708 (2.3) | 2,414 (2.31) | |
| Black | 3,258 (10.58) | 8,621 (825) | |
| Hispanic | 2,478 (8.05) | 6,569 (6.29) | |
| Other | 2,513 (8.16) | 12,715 (12.17) | |
| Pacific Islander | 43 (0.14) | 117 (0.11) | |
| Unknown | 12,300 (39.96) | 44,079 (42.21) | |
| White | 9,096 (29.55) | 28,959 (27.73) | |
| Ventricular Rate | 82.4 (82.2-82.6) | 77.8 (77.7-77.9) | <0.0001 |
| Atrial Rate | 99.1 (98.4-99.8) | 84.5 (84.2-84.8) | <0.0001 |
| PR Interval | 170.1 (169.7-170.5) | 163.8 (163.6-164.0) | <0.0001 |
| QTc Interval | 464.1 (463.6-464.7) | 446.2 (445.9-446.4) | <0.0001 |
| | External Validation Cohort | | |
| Patients | 1,783 | 11,649 | |
| Echo-ECG Pairs | 8,828 | 47,990 | |
| Age | 67.2 (66.9-67.5) | 67.3 (67.1-67.4) | 0.06 |
| Gender | | | <0.0001 |
| Male | 1,067 (59.84) | 5,881 (50.49) | |
| Female | 716 (40.16) | 5,768 (49.51) | |
| Race | | | <0.0001 |
| American Indian | — | — | |
| Asian | — | 35 (0.3) | |
| Black | 289 (16.21) | 1,629 (13.98) | |
| Hispanic | 33 (1.85) | 159 (1.36) | |
| Other | 502 (28.15) | 3,775 (32.41) | |
| Pacific Islander | — | — | |
| Unknown | 578 (32.92) | 3,483 (29.90) | |
| White | 368 (20.64) | 2,564 (22.01) | |
| Ventricular Rate | 86.0 (85.0-86.9) | 79.9 (79.6-80.3) | <0.0001 |
| Atrial Rate | 104.5 (101.5-107.5) | 86.4 (85.6-87.2) | <0.0001 |
| PR Interval | 171.8 (170.0-173.6) | 166.9 (164.7-169.2) | <0.0001 |
| QTc Interval | 473.6 (471.5-475.8) | 451.9 (451.2-452.6) | <0.0001 |

45

TABLE III

| | | Performance at LVEF classification for evaluation prevalence, area under receiving operating characteristic curve (AUROC), area under precision recall curve (AUPRC), sensitivity, and specificity, where values are percent or mean with sensitivity and specificity being derived using Youden's index. | | | | |
| --- | --- | --- | --- | --- | --- | --- |
| Outcome | Cohort | Evaluation Prevalence (%) | AUROC | AUPRC | Sensitivity | Specificity |
| LVEF ≤ 35% | Internal Testing | 9.22 | 0.95 | 0.68 | 0.94 | 0.83 |
| | External Validation | 23.07 | 0.95 | 0.88 | 0.88 | 0.87 |
| LVEF ≤ 40% | Internal Testing | 12.52 | 0.94 | 0.72 | 0.89 | 0.83 |
| | External Validation | 25.85 | 0.94 | 0.88 | 0.87 | 0.85 |
| LVEF 40-50% | Internal Testing | 10.73 | 0.82 | 0.33 | 0.84 | 0.65 |
| | External Validation | 14.87 | 0.73 | 0.29 | 0.78 | 0.57 |
| LVEF > 50% | Internal Testing | 76.74 | 0.89 | 0.96 | 0.81 | 0.80 |

US 12,642,512 B2

19                                                                          20

TABLE III-continued

Performance at LVEF classification for evaluation prevalence, area under receiving
operating characteristic curve (AUROC), area under precision recall curve
(AUPRC), sensitivity, and specificity, where values are percent or mean with
sensitivity and specificity being derived using Youden's index.

| Outcome | Cohort | Evaluation Prevalence (%) | AUROC | AUPRC | Sensitivity | Specificity |
|---------|--------|---------------------------|-------|-------|-------------|-------------|
|         | External Validation | 59.28 | 0.87 | 0.90 | 0.84 | 0.81 |

Model performance for classification tasks was primarily evaluated through analysis of the area under receiver operating characteristic curve (AUROC) and area under precision recall curve (AUPRC) metrics. Additionally, the diagnostic platform considered Youden's index in computing threshold-dependent metrics. Youden's index (also called "Youden's J statistic") is a single statistic that captures the performance of a dichotomous diagnostic test. For the regression task, the diagnostic platform used mean absolute error ("MEA") as the evaluation metric.

To evaluate cumulative incidence by model prediction, the diagnostic platform fit a Kaplan-Meier estimator to the time difference between the first model-derived false positive/true negative of low LVEF value and the first echocardiographically derived low LVEF value. As part of a baseline comparison, the diagnostic platform also implemented processing and modeling pipelines for traditional statistical approaches geared toward prediction of low LVEF values.

Performance was examined across several different metrics and verticals. As an example, the diagnostic platform established performance of an NLP algorithm in labeling RV abnormalities. Specifically, the diagnostic platform can build a rule-based NLP algorithm to identify RVSD and RVD outcomes from each reports. To assess the validity of this procedure, human-generated labels for these echo reports were compared with algorithm-generated labels and then quantified in terms of the number of correctly classified labels, incorrectly classified labels, and missed labels.

There were 420 outcomes included in review. For RV function, the model was able to correctly classify 404 outcomes, did not predict a label for 13 outcomes, and incorrectly classified 3 outcomes. For RV size, the model was able to correctly classify 402 outcomes, did not predict a label for 17 outcomes, and incorrectly classified 1 outcome. Within detected outcomes, the model achieved an overall accuracy of 99.7 percent for extraction of either RV function or RV size.

Additionally, the diagnostic platform built a model to classify LVEF in terms of the following clinically relevant categories: ≤40 percent, >40 percent and ≤50 percent, and >50 percent from an ECG. The outcome distribution for the LVEF dataset and experiments is provided in Table II.

Overall, the model performed extremely well at detecting patents with LVEF values of ≤40 percent for internal testing (12.52 percent prevalence) and external validation (25.85 percent prevalence) with AUROC values of 0.94 (95% Confidence Interval: 0.94-0.95) in each case. This trend was maintained for the precision recall curves as well, with AUPRC values of 0.72 (95% Confidence Interval: 0.71-0.73) for internal testing, increasing to 0.88 (95% Confidence Interval: 0.88-0.89) for external validation.

Similar results were observed for detecting patients with LVEF values of >50 percent. For internal testing (76.7 percent prevalence), the model achieved an AUROC of 0.89

(95% Confidence Interval: 0.89-0.89), and this was maintained for external validation (59.3 percent prevalence) at 0.87 (95% Confidence Interval: 0.87-0.88). AUPRC values were also exceptional at 0.96 (95% Confidence Interval: 0.96-0.96) for internal testing and 0.90 (95% Confidence Interval: 0.90-0.91) for external validation.

Performance was lower for LVEF values >40 percent and ≤50 percent. For the internal testing dataset (10.83 percent prevalence), the model achieved an AUROC of 0.82 (95% Confidence Interval: 0.81-0.83). For the external validation dataset, the model achieved an AUROC of 0.73 (95% Confidence Interval: 0.72-0.74). AUPRC values were 0.33 (95% Confidence Interval: 0.30-0.36) for the internal testing dataset and 0.29 (95% Confidence Interval: 0.28-0.31) for the external validation dataset.

Figure 10:
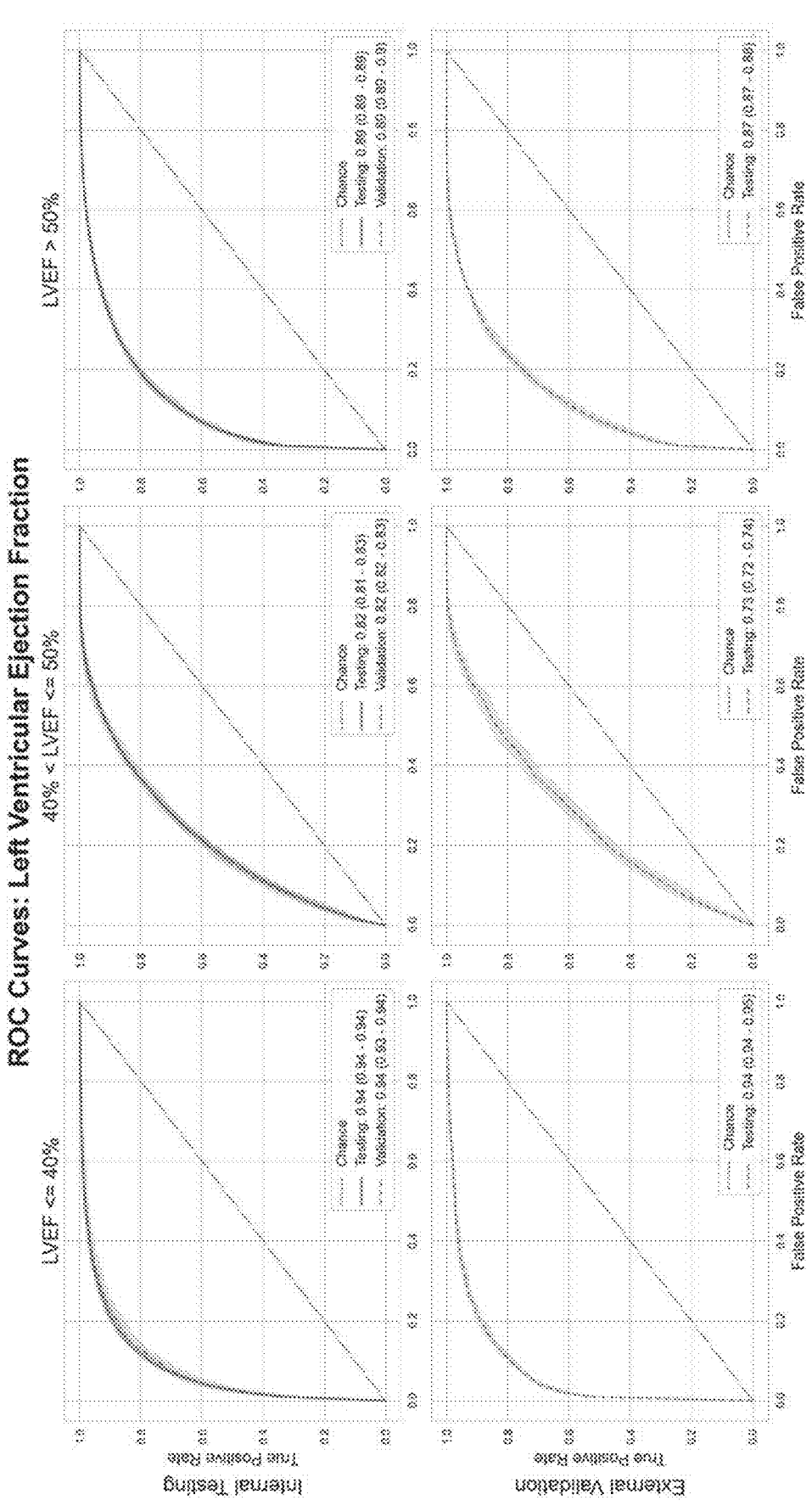
FIG. 10 includes receiver operating characteristic curves—as can be used for classification—for LVEF values in three different ranges.
Figure 11:
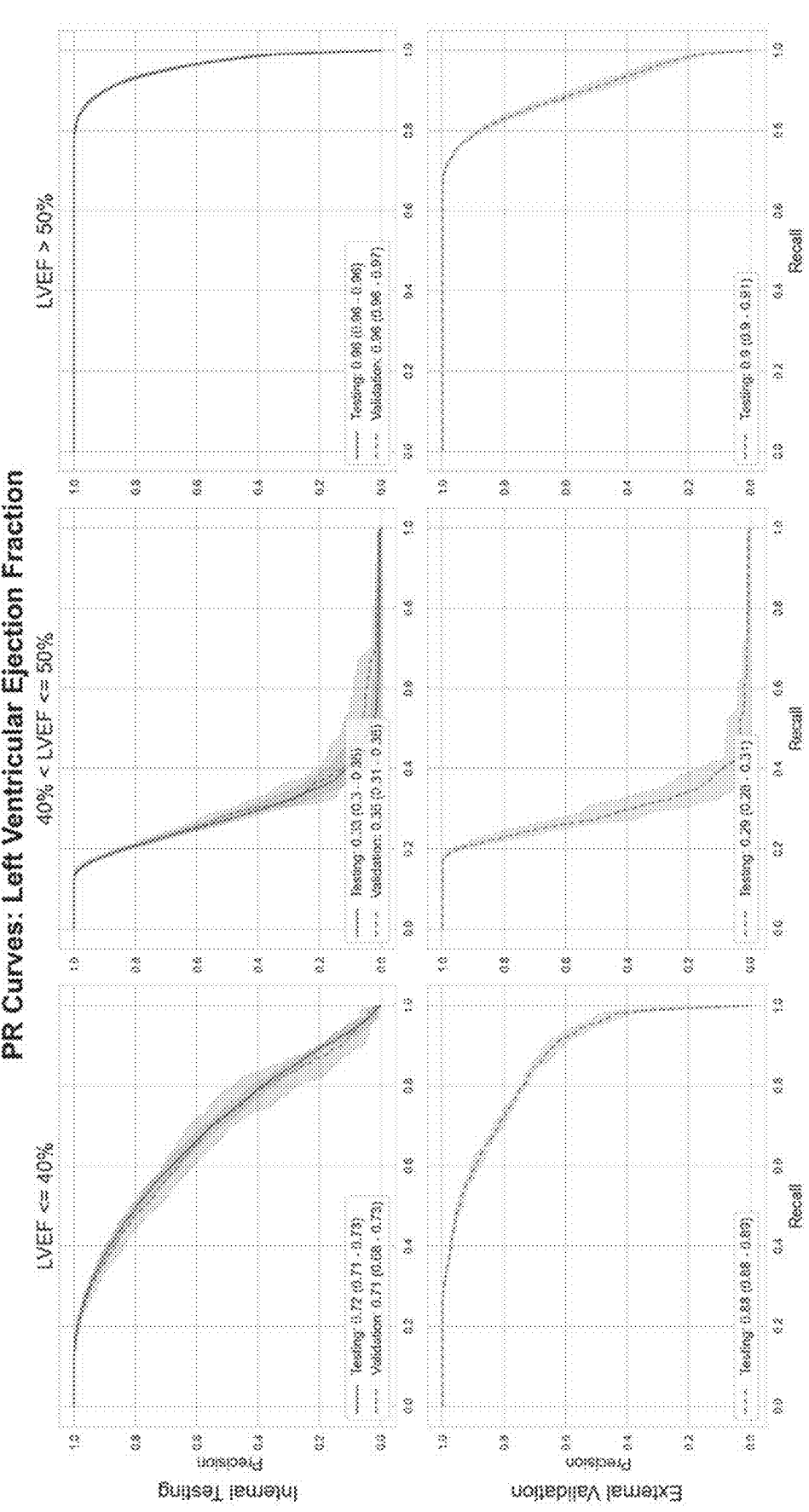
FIG. 11 shows precision recall curves that correspond to those receiver operating characteristic curves shown in FIG. 10.
Figure 12:
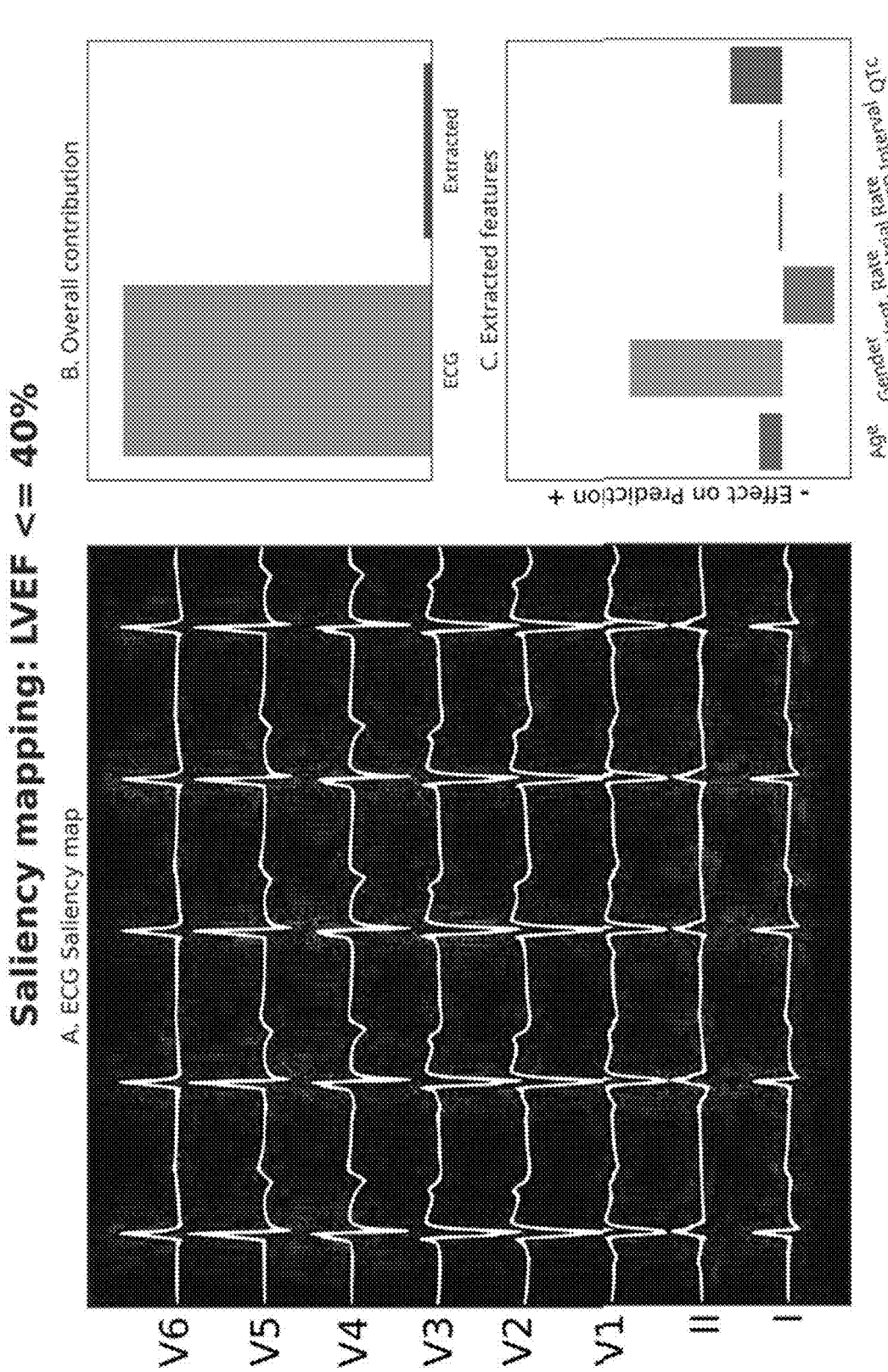
FIG. 12 includes interpretability plots (also called "explainability plots") for LVEF prediction using a framework that highlights QRS complexes for prediction of each LVEF-related outcome.

FIG. 10 includes receiver operating characteristic curves—as can be used for classification—for LVEF values in three different ranges. Specifically, the upper row shows performance for each outcome in the internal testing cohort, while the lower row shows performance for each outcome in the external validation cohort. Meanwhile, FIG. 11 shows precision recall curves that correspond to those receiver operating characteristic curves shown in FIG. 10. FIG. 12 includes interpretability plots (also called "explainability plots") for LVEF prediction using a framework that highlights QRS complexes for prediction of each LVEF-related outcome. The relative importance of the extracted features was found to be variable across the patient population. For example, gender may have a larger effect on prediction than age and atrial rate as shown in FIG. 12.

Figure 13:
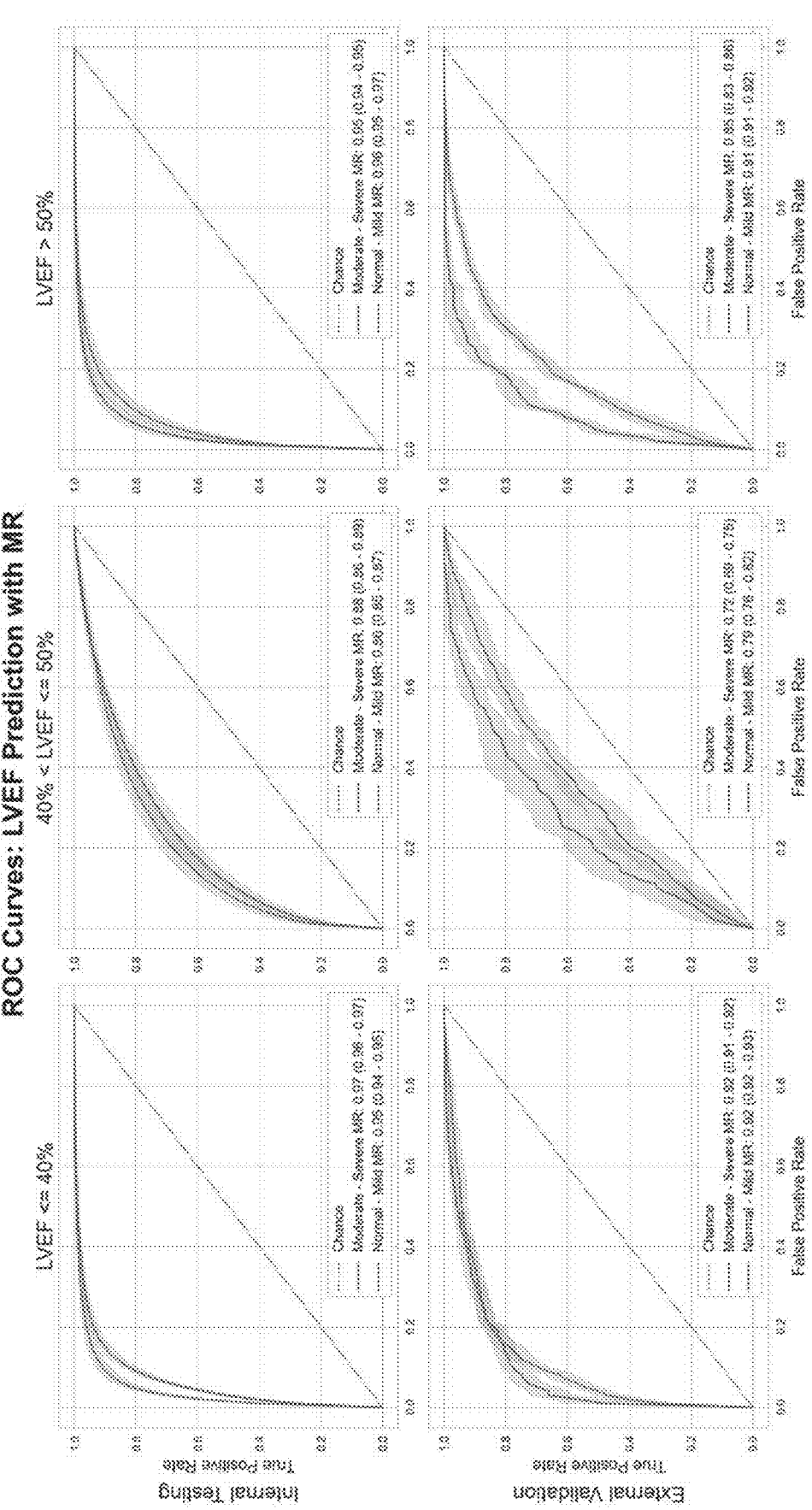
FIG. 13 includes receiver operating characteristic curves for LVEF values across different severities of mitral regurgitation ("MR"), where the upper row shows performance across the internal testing cohort while the lower row shows performance across the external validation cohort.
Figure 14:
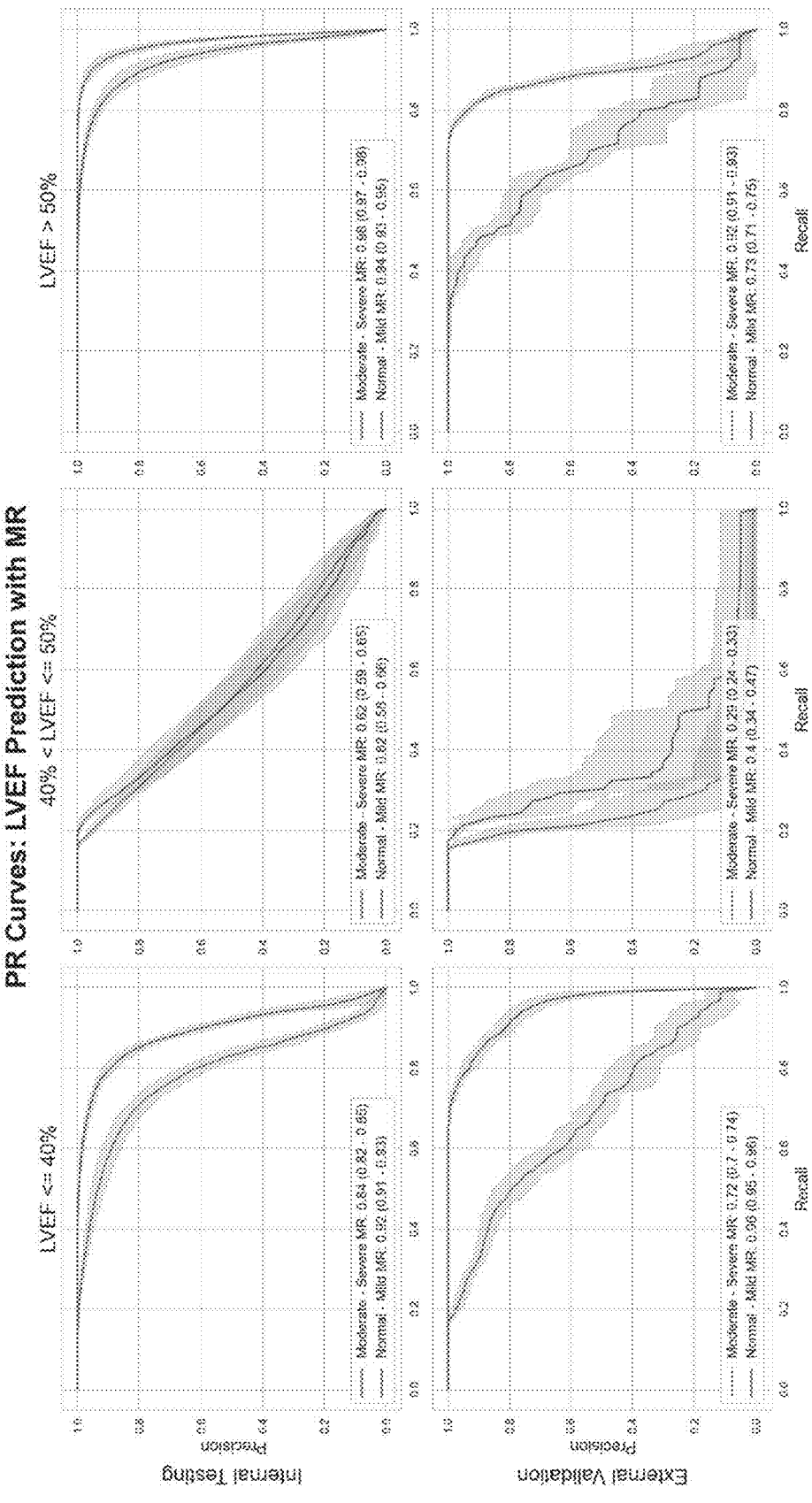
FIG. 14 shows precision recall curves that correspond to those receiver operating characteristic curves shown in FIG. 13.

Performance of the model was maintained when tested against varying severities of MR, with better performance observed when tested against normal-to-mild MR. FIG. 13 includes receiver operating characteristic curves for LVEF values across different severities of MR, where the upper row shows performance across the internal testing cohort while the lower row shows performance across the external validation cohort. FIG. 14 shows precision recall curves that correspond to those receiver operating characteristic curves shown in FIG. 13.

Figure 15:
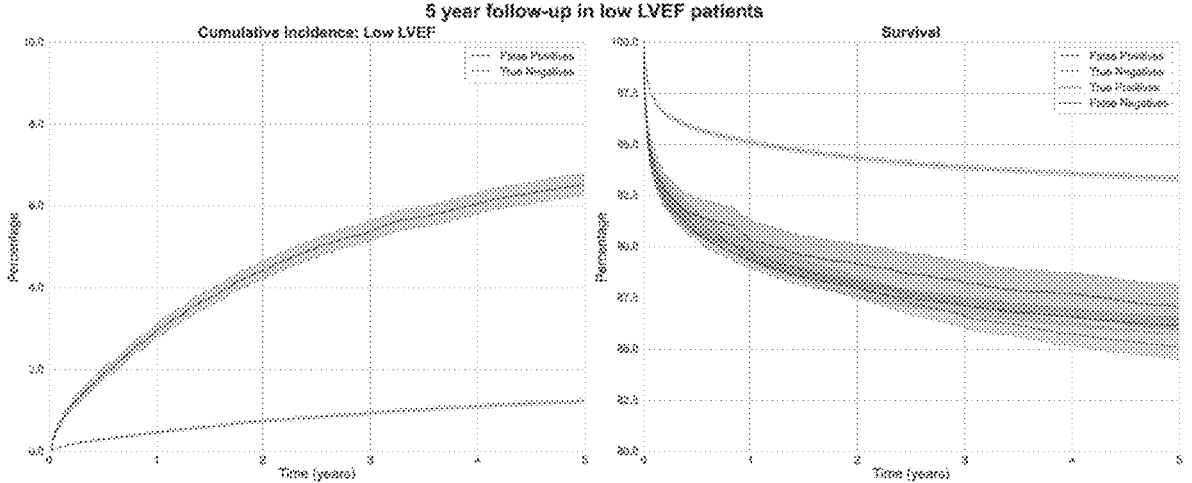
FIG. 15 illustrates the cumulative incidence of low LVEF (left) and survival (right) over a five-year follow-up period in low LVEF (i.e., LVEF≤40 percent) patients per prediction type.

As mentioned above, the diagnostic platform also applied Youden's index to predictions output by the model to derive false positives and true negatives. It has been found that cumulative incidence of low LVEF in a five-year follow-up period after the first prediction was higher in patients labeled false positive than those patients labeled true negative. It was also found that survival was higher in true negatives over the other classes of patients. FIG. 15 illustrates the cumulative incidence of low LVEF (left) and survival (right) over a five-year follow-up period in low LVEF (i.e., LVEF≤40 percent) patients per prediction type.

In a separate experience designed for detecting patients with an LVEF≤35 percent, the model performed exceedingly well in internal testing (9.22 percent prevalence), with an AUROC of 0.95 (95% Confidence Interval: 0.95-0.95) and an AUPRC of 0.68 (95% Confidence Interval: 0.67-0.69). These results were maintained for the external validation dataset (23.07 percent prevalence), with an AUROC of 0.95 (95% Confidence Interval: 0.95-0.95) and an AUPRC of 0.88 (95% Confidence Interval: 0.87-0.89).

Figure 16:
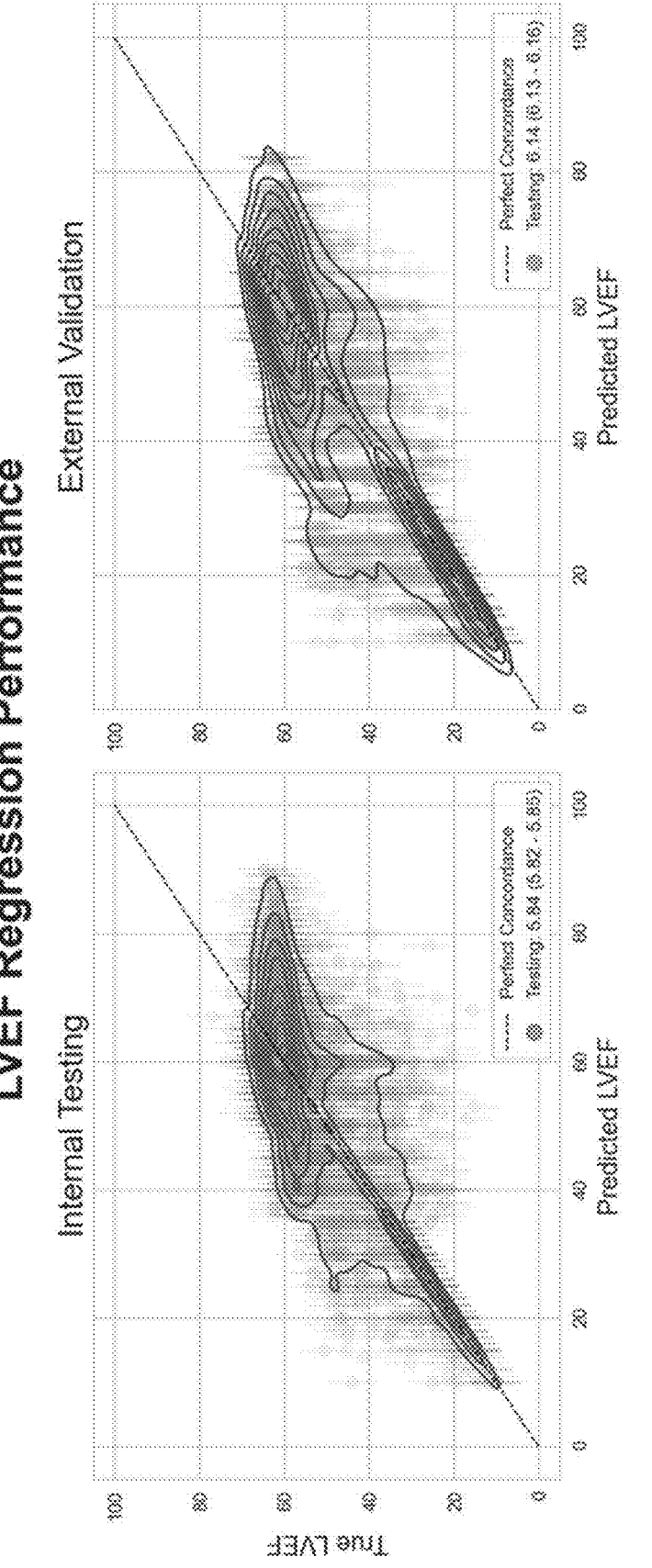
FIG. 16 includes a scatterplot showing the relationship between the predicted and actual LVEF values for a dataset.

In order to establish the performance of LVEF regression, the diagnostic platform constructed another model—specially a DL model—to predict the exact value of LVEF from an echo-ECG pair within a regression framework. With the internal testing dataset, the MAR was 5.84 percent (95% Confidence Interval: 5.82-5.85 percent). For the external validation dataset, the MAR was 6.14 percent (95% Confidence Interval: 6.13-6.16 percent). A scatterplot showing the relationship between the predicted and actual LVEF values for the overall dataset is shown in FIG. 16. FIG. 16 includes contour lines that show the density of the predicted LVEF values versus the actual LVEF values that serve as the ground truth around the line of perfect concordance.

Figure 17:
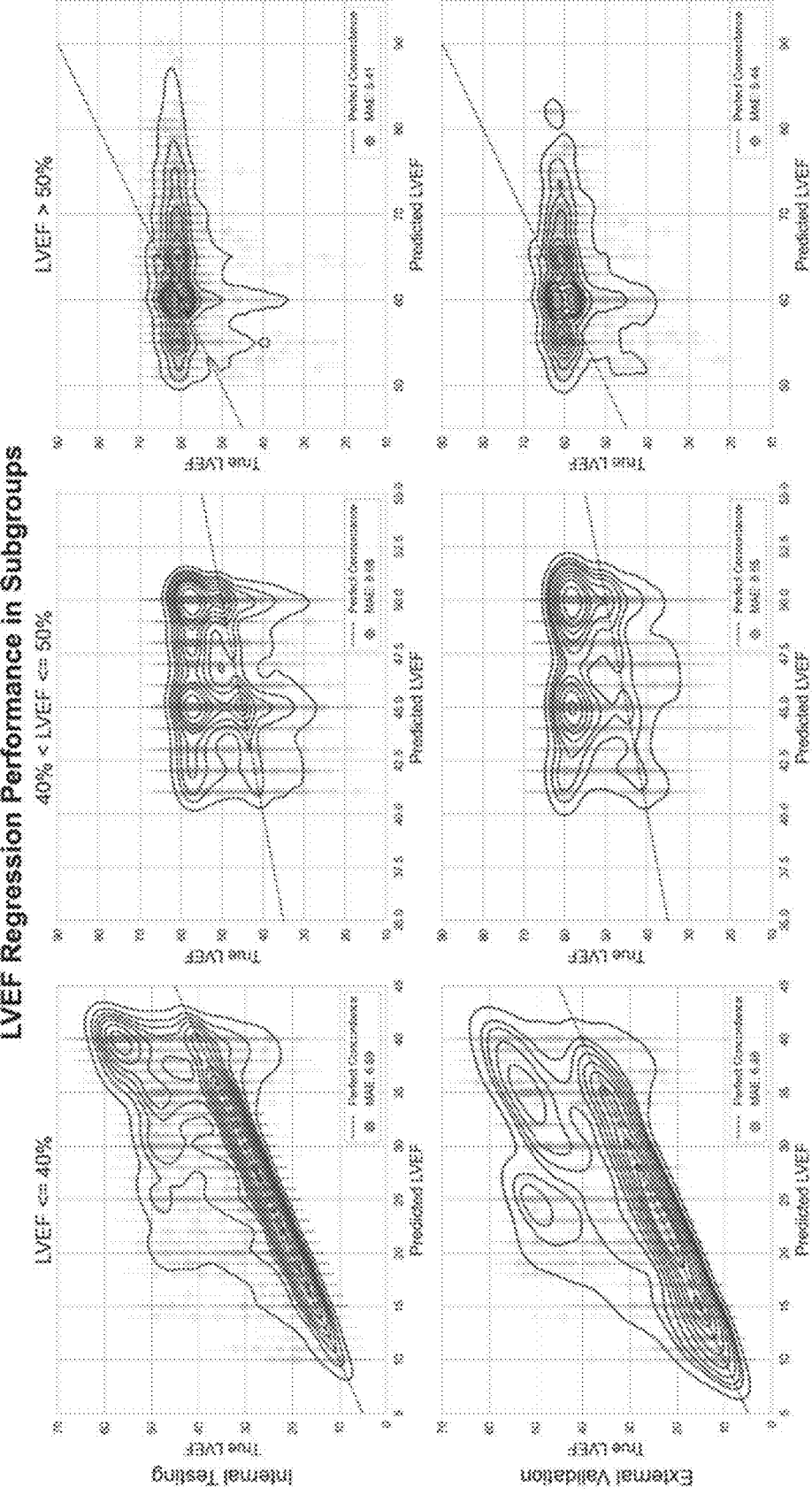
FIG. 17 includes scatter plots showing the LVEF regression performance across different subgroups.

The diagnostic platform evaluated the performance of the DL model within clinically relevant LVEF subgroups. In the first subgroup of echo-derived LVEF values that are less than 40 percent, the MAE for the regression model was 6.69 percent in internal testing and 6.46 percent in external validation. In the second subgroup of echo-derived LVEF values that are between 40 and 50 percent, the MAE was greater at 8.08 percent in internal testing and 8.55 percent in external validation. In the third subgroup of echo-derived LVEF values that are greater than 50 percent, the DL model achieved a MAE of 5.41 percent in internal testing and 5.44 percent in external validation. FIG. 17 includes scatter plots showing the LVEF regression performance across these subgroups. Like FIG. 16, the contour lines show the density of the predicted LVEF values versus the actual LVEF values that serve as the ground truth around the line of perfect concordance.

Figure 18:
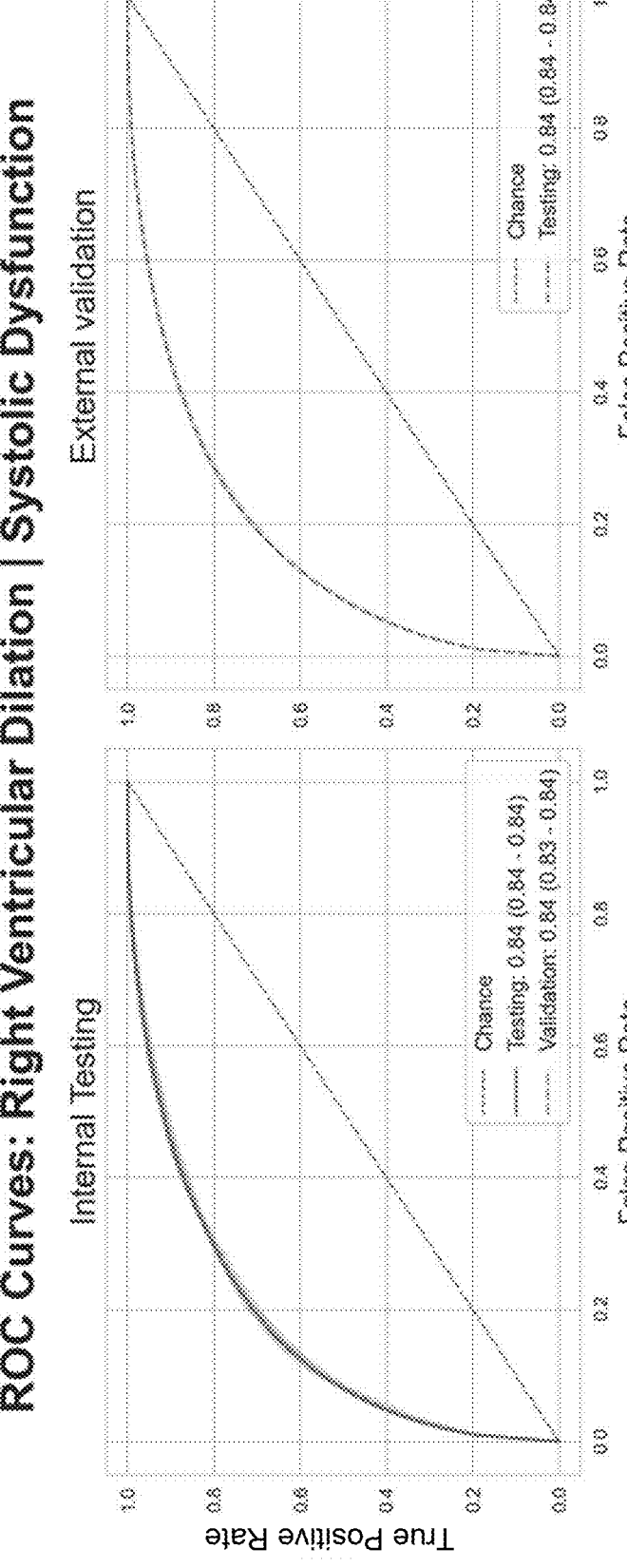
FIG. 18 illustrates the receiver operating characteristic curves for RVSD and RVD classification, with the false positive rate plotted for the internal testing dataset (left) and external validation dataset (right).
Figure 19:
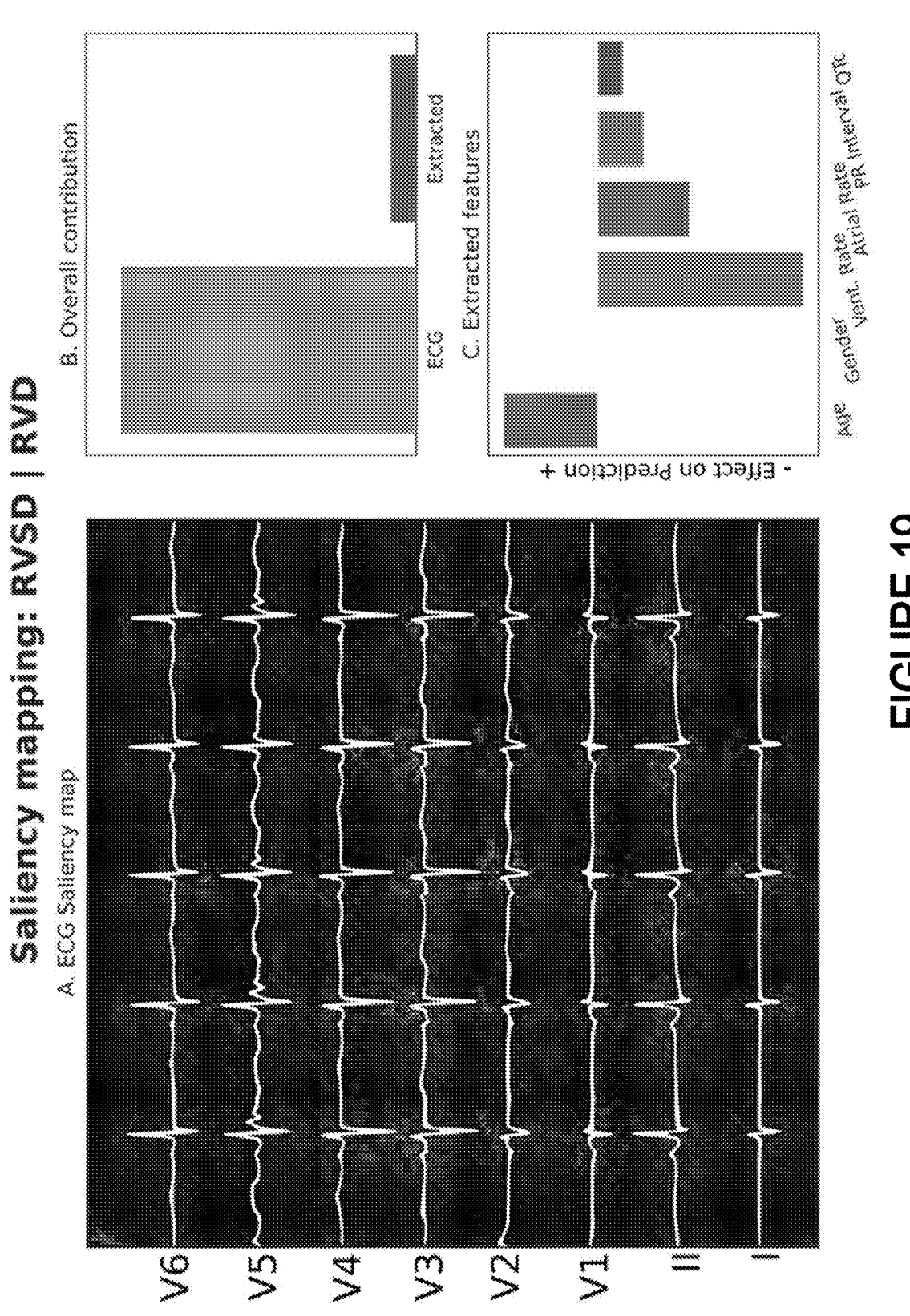
FIG. 19 includes plots that are created for explainability, highlighting QRS complexes for prediction of composite outcomes.

In order to establish the performance of RVSD and RVD classification, the diagnostic platform constructed another model—specifically another DL model—to predict either RVSD or RVD from ECG data in internal testing (32.44 percent prevalence) and external validation (15.53 prevalence). This other DL model achieved robust performance with an AUROC of 0.84 (95% Confidence Interval: 0.84-0.84) in internal testing, maintained in external validation at 0.84 (95% Confidence Interval: 0.84-0.84). Similar results were achieved with respect to AUPRC, with values of 0.67 (95% Confidence Interval: 0.66-0.67) in internal testing and 0.55 (95% Confidence Interval: 0.54-0.55) in external validation. FIG. 18 illustrates the receiver operating characteristic curves for RVSD and RVD classification, with the false positive rate plotted for the internal testing dataset (left) and external validation dataset (right). Information regarding performance across the internal testing cohort and external validation cohort can be found in Table IV. Meanwhile, plots created using the aforementioned framework for explainability, again highlighting QRS complexes for prediction of composite outcomes, is shown in FIG. 19.

Figure 20:
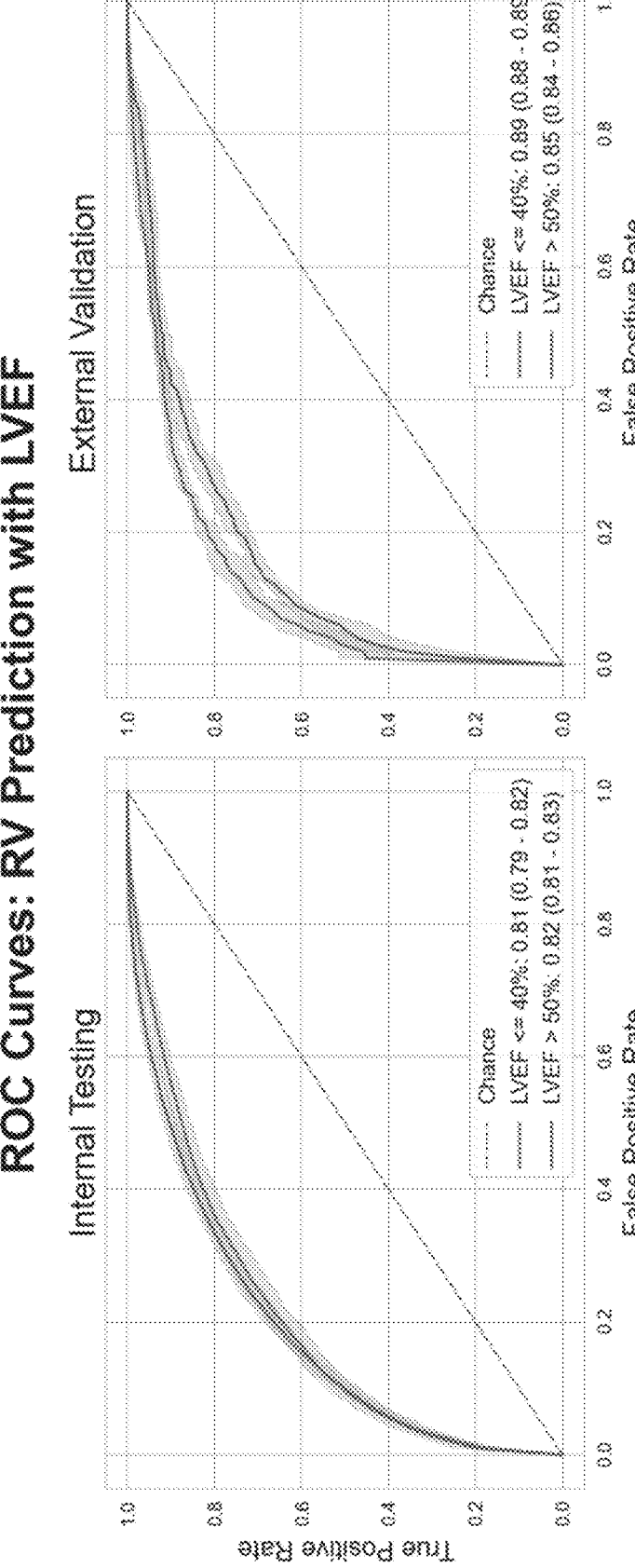
FIG. 20 includes receiver operating characteristic curves for RVSD and RVD predictions in the presence of low (i.e., ≤40 percent) or near normal (i.e., <50 percent) LVEF values.
Figure 21:
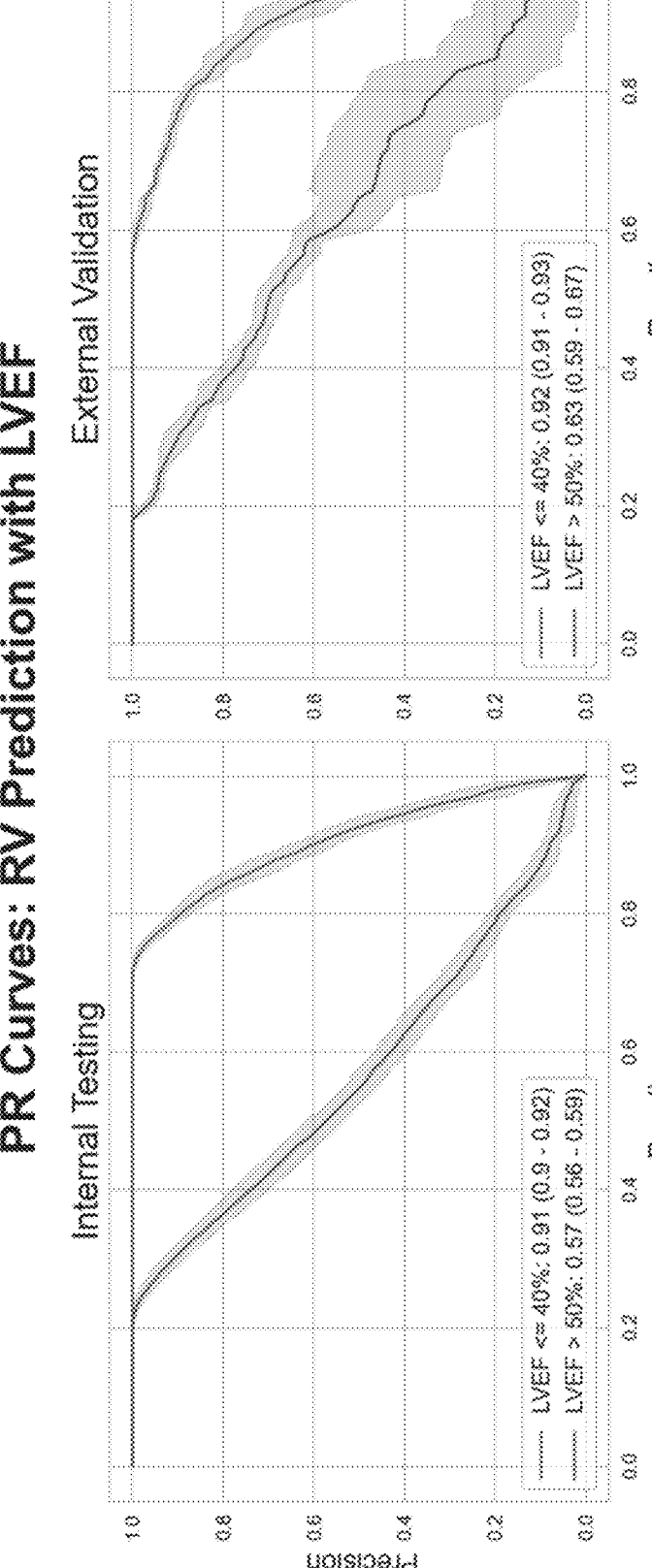
FIG. 21 shows precision recall curves that correspond to those receiver operating characteristic curves shown in FIG. 20.

AUPRC values output by this other DL model, when evaluated in the presence of low LVEF, were seen to be substantially increased over those in the presence of normal LVEF. FIG. 20 includes receiver operating characteristic curves for RVSD and RVD predictions in the presence of low (i.e., ≤40 percent) or near normal (i.e., <50 percent) LVEF values. FIG. 21 shows precision recall curves that correspond to those receiver operating characteristic curves shown in FIG. 20.

TABLE IV

| Performance at RVSD and RVD composite classification, where values are percent or mean with sensitivity and specificity being derived using Youden's index. | | | | |
| --- | --- | --- | --- | --- |
| Evaluation Prevalence (%) | AUROC | AUPRC | Sensitivity | Specificity |
| Internal Testing | 32.44 | 0.84 (0.84-0.84) | 0.66 (0.66-0.67) | 0.75 (0.73-0.76) | 0.77 (0.75-0.78) |
| External Validation | 15.54 | 0.84 (0.84-0.84) | 0.55 (0.54-0.55) | 0.77 (0.76-0.78) | 0.75 (0.74-0.76) |

Figure 22:
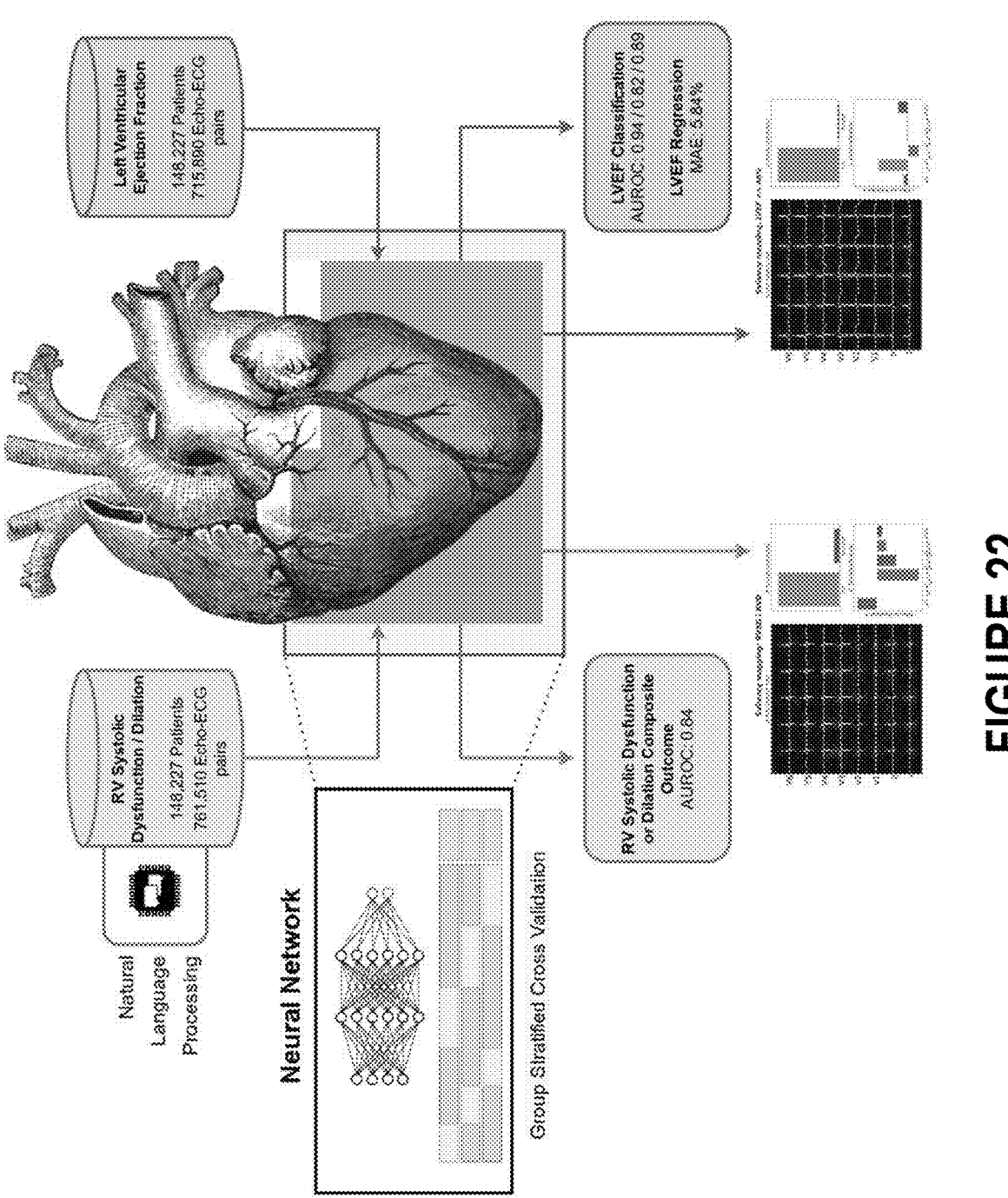
FIG. 22 includes a high-level summary of a workflow for processing and then analyzing electrocardiogram data using a neural network.

Using over 700,000 ECGs corresponding to approximately 150,000 patients from a diverse cohort of patients in the New York City area, the diagnostic platform developed, evaluated, and then validated multimodal DL models capable of discerning the contractile state of the left and right ventricles. An accurate NLP pipeline for extracting outcomes from free-text echo reports was created, and a multimodal explainability framework to highlight which parts of ECGs are more salient for each outcome was developed. By highlighting the salient parts of ECGs, the relationships between demographic information and imaging data can be more readily derived. FIG. 22 includes a high-level summary of a workflow for processing and then analyzing ECG data using a neural network. Specifically, the workflow illustrates how the diagnostic platform can perform DL-based identification of left and right ventricular dysfunction through analysis of ECG data.

Work on LVEF extraction from ECGs has historically been limited to classification of LVEF values that are ≤35 percent. Here, however, the classification framework is extended to clinically pertinent ranges of ≤40 percent, 40 to 50 percent, and >50 percent to be able to surface issues that may have prognostic implications. For example, the difference between an LVEF of 41 percent and an LVEF of 71 percent is hemodynamically and clinically significant. In additional testing, performance at detection of LVEF values that are ≤35 percent results in an AUROC of 0.95 across the diverse patient population. Not only did the models described herein outperform traditional statistical approaches that rely on extracting ECG features to detect low LVEF values, but the models also do not require manual feature selection. Simply put, an additional benefit of utilizing DL CNNs is the lack of a requirement of manual feature selection. While manual feature annotation may outperform DL CNNs in some situations due to strong inductive bias, manual action poses significant limitations due to the strict requirement on expert domain knowledge. Further, patterns that represent an outcome of interest may not be apparent to humans at all.

Finally, higher cumulative incidence of LVEF values that are ≤40 percent over a five-year follow-up period in false positives over true negatives indicates the model's ability to gauge patient severity. Using the model, such patients may be diagnosed earlier in the clinical course, with appropriate threshold selection depending on the needs of users of the diagnostic platform.

Threshold selection also has a role in the use and deployment of such models. By setting the classification threshold to an appropriately low value, such models can be used as screening tools for low LVEF values in asymptomatic patients, at the cost of some false positives. For LVEF values≤40 percent, a sensitivity of 90 percent was achieved at a specificity of 82.5 percent at an AUROC of 0.94.

Clinical guidelines, which segment patients based on LVEF values, assume that a single set of classification boundaries is broadly applicable to the entire population. However, normal variation in echo-derived baseline values is expected secondary to patient demographics. A regression-based framework reduces the risk of misclassification. By employing LVEF regression as discussed herein, the value of screening ECGs can be dramatically enhanced—even in low-risk groups—as indications of disease can be surfaced earlier. The regression-based framework may also be more useful for evaluation of LVEF in a longitudinal setting in which LVEF changes over time. Further, the regression-based framework can be independent of changes in management guidelines, leading to greater resiliency.

Internal validation alone may not guarantee model quality. Biases within the training dataset that help performance may not translate to external cohorts. It follows that external validation is important to assess how generalizable a model is. It has been found that for evaluation of LVEF, there is minimal-to-low change in performance in going from internal to external validation.

Diagnoses of RV dysfunction using DL on ECG data is a novel approach to surfacing insights into cardiac health. While the left and right ventricles are inextricably linked, using LVEF as a predictor in a univariate logistic regression model for predicting composite RVSD and RVD outcomes only achieves an AUROC of 0.71 (95% Confidence Interval: 0.70-0.72). The aforementioned models perform robustly for the detection of compromised RV state at an AUROC of 0.84 (95% Confidence Interval: 0.83-0.84). In addition, the high AUPRC values in the presence of LVEF≤40 percent indicate that such models are suited for tracking RV involvement secondary to heart failure with reduced ejection fraction ("HFrEF"). Once again, the aforementioned models translated well to external validation. In this experiment, the decision was made to not stratify RV disease according to severity, so as to allow for early detection of disease. However, the aforementioned models could be trained to stratify RV disease if the context warrants as much (and sufficient training data and computational resources are available). Depending on clinical context, this approach may be adjusted to more severe disease. For example, stratification may provide greater value as disease severity increases. Performance in this context will likely increase because there is a greater difference between the normal and diseased cases.

Figure 23:
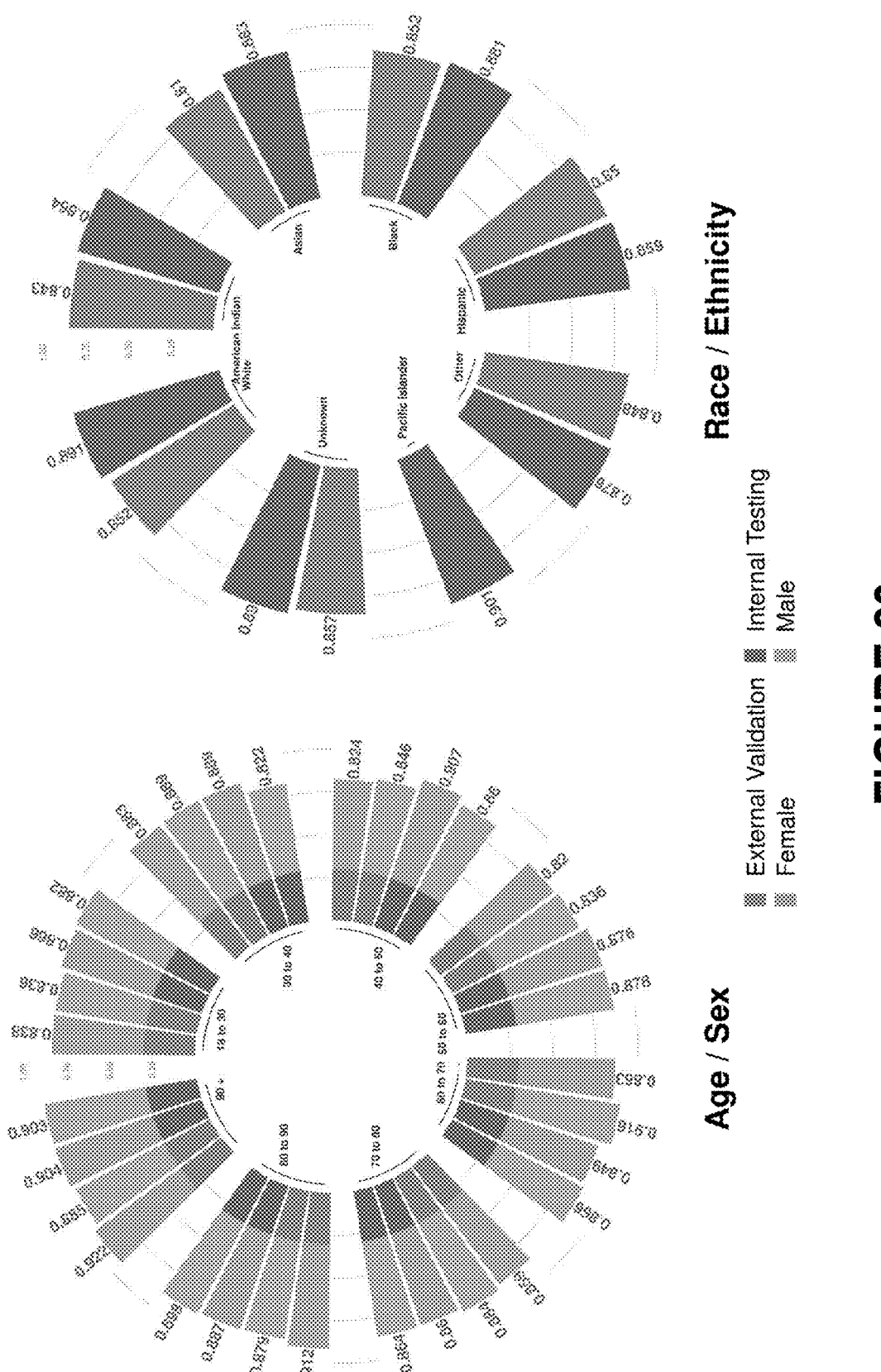
FIG. 23 illustrates how datasets used for internal testing and external validation are diverse across age, sex, and ethnicity.

Classification performance of the aforementioned models was also evaluated across diverse populations. FIG. 23 illustrates how the datasets used for internal testing and external validation are diverse across age, sex, and ethnicity. It has been found that model performance is consistent across different subgroups of the population, in line with overall performance.

B. Guided Diagnosis of Transvalvular Flow State in Aortic Stenosis

Aortic stenosis ("AS") is a chronic, progressive narrowing of the opening of the aortic valve. AS is most commonly caused by cumulative age-related calcium deposition on the aortic valve, with an estimated 3.4 percent prevalence in adults over 75 years of age. Contingent upon mean pressure gradient ("MPG") across the aortic valve and LVEF, severe AS can be subtyped into (i) high-gradient severe AS, (ii) classical low-flow, low-gradient severe AS, (iii) paradoxical low-flow, low-gradient AS, and (iv) paradoxical normal-flow, low-gradient AS. Without adequate management, chronic increase in afterload eventually leads to left ventricular decompensation with regression of the normal flow state into a low flow state. Conversely, early diagnosis and treatment—for example, with surgical aortic valve replacement ("SAVR") or transcatheter aortic valve replacement ("TAVR") procedures—is associated with better overall outcomes.

The diagnostic mainstay for AS is transthoracic echocardiography, which is generally unsuitable for routine screening due to its relatively high time and personnel demands. Conversely, the ECG is a non-invasive, inexpensive, and ubiquitous modality—bounded in diagnostic utility by the extend of healthcare professionals' reading capabilities. As mentioned above, DL relates to the application of neural networks to detect patterns in complex data that may be largely, if not entirely, hidden to the human eye. DL is especially effective at extracting additional clinical context from investigations into physiological data such as ECG data.

Though it is a valvular disease, AS can induce electrocardiographic changes concomitant with cardiac remodeling caused by increased left ventricular afterload and impaired systolic and diastolic function. While efforts have been made to predict severe AS through analysis of ECG data, those efforts were largely unproductive. Given the prevalence of AS—and the benefits of early diagnosis and intervention—the diagnostic platform may leverage the granular information contained in echo reports to develop more precise diagnostic methods.

Figure 24B:
Figure 24C:
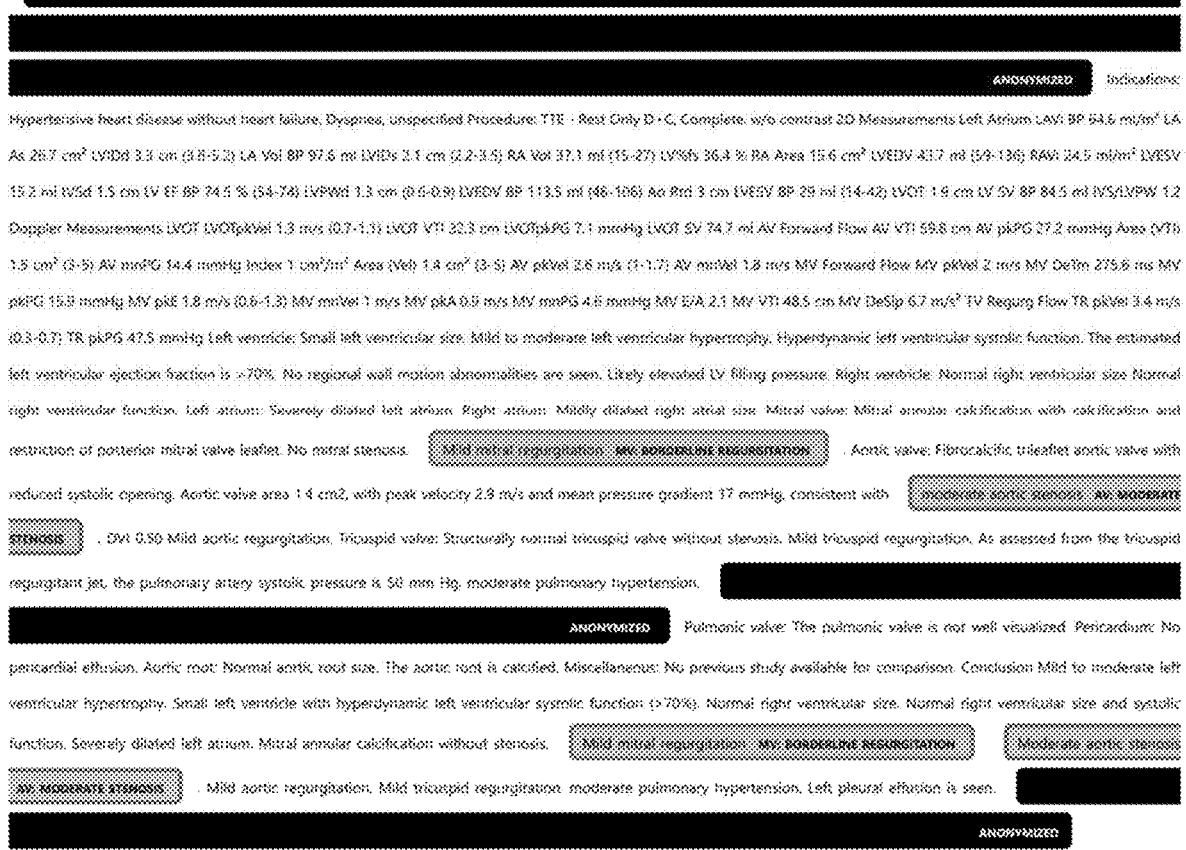

Diagnosing valvular diseases is procedurally similar to diagnosing ventricular function. As such, the diagnostic platform may develop and then train a model to diagnose valvular disease in a manner similar to that set forth above. The primary differences are within the NLP pipeline used during the training stage. The diagnostic platform can develop and then implement different rules in order to identify terms and phrases indicative of valvular diseases in echo reports. FIG. 24A-C include examples of anonymized, annotated echo reports that have been processed using those rules developed for AS.

Specifically, the diagnostic platform developed a neural network that is trained on ECG data to classify subtypes of severe AS. To establish performance, a retrospective study was conducted with ECG data acquired from multiple healthcare facilities in the New York City area that serve a diverse population. The ECG data was acquired in the form of echo reports. NLP was used to extract values for stroke volume, body surface area, LVEF, aortic valve area, and aortic valve MPG from the unstructured text of the echo reports. Extracted values were used to diagnose the presence and severity of AS, in addition to the contractile state of the heart. The diagnostic platform paired the echo reports to ECGs performed within a predetermined interval of time (e.g., ±7 days, 10 days, 15 days, etc.), and then the diagnostic platform trained and tested a CNN. The diagnostic platform then stratified data by unique identifiers within a Group K fold cross-validation to ensure no overlap of patients between the training and validating datasets.

Figure 25:
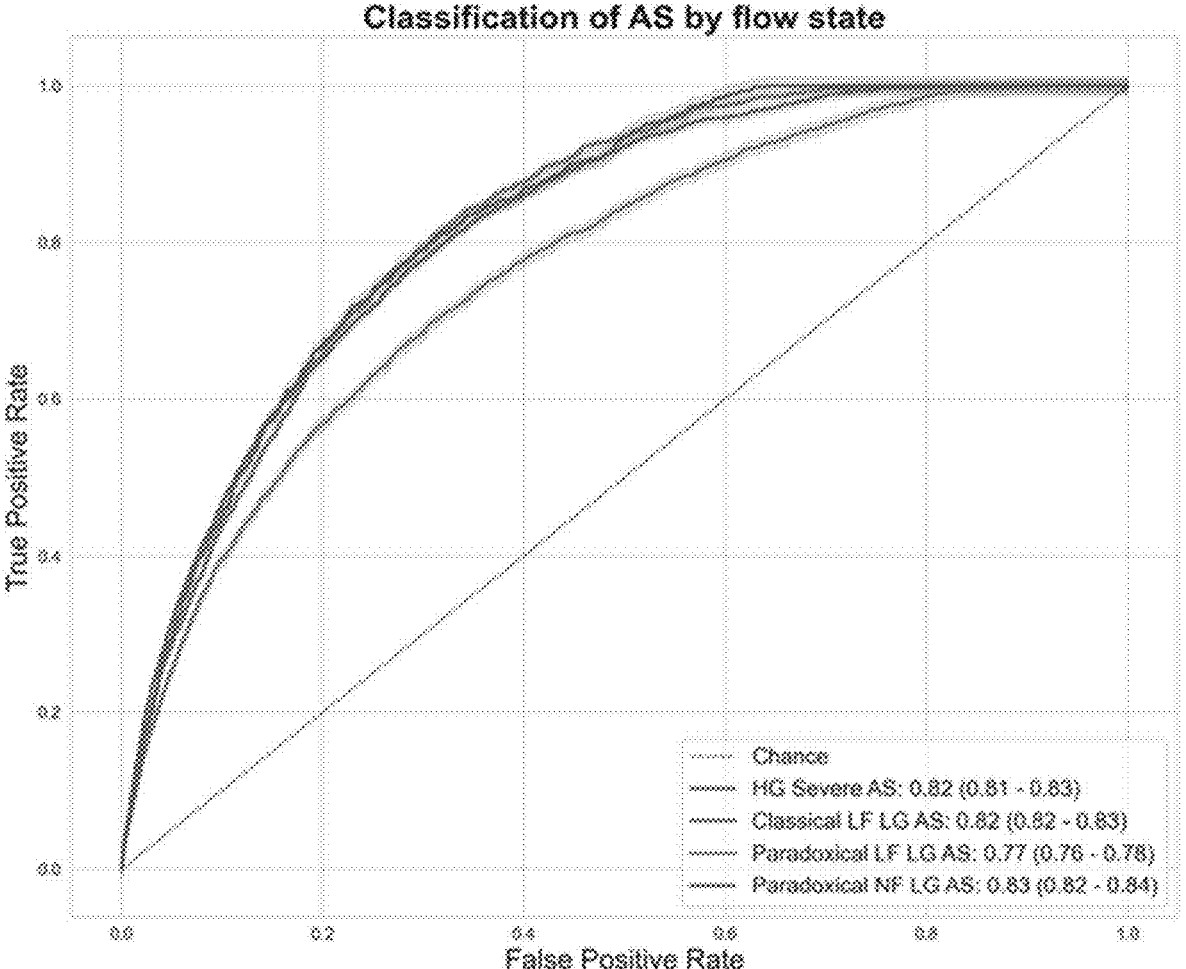
FIG. 25 illustrates the true positive rate against the false positive rate for the aforementioned classifications of severe aortic stenosis.

The diagnostic platform obtained 304,002 echo reports for 130,763 patients corresponding to the interval of time between January 2008 and July 2020. Data extracted from these echo reports were paired with 729,768 ECGs. For classification of flow state with severe AS into high-gradient severe (12,965 ECGs), classical low-flow, low-gradient severe (10,057 ECGs), paradoxical low-flow, low-gradient severe (11,542 ECGs), and paradoxical normal-flow, low-gradient severe (4,157 ECGs), the AUROC values were 0.82 (95% Confidence Interval: 0.81-0.83), 0.82 (95% Confidence Interval: 0.82-0.83), 0.77 (95% Confidence Interval:

0.76-0.78), and 0.83 (95% Confidence Interval: 0.82-0.84), respectively. FIG. 25 illustrates the true positive rate against the false positive rate for the aforementioned classifications of severe AS. Further, it has been found that model performance was maintained when stratifying patients by severe MR.

The robust performance of the CNN is encouraging for use in live environments where transthoracic echocardiography is not practical or possible-supporting the role of DL as applied to the data generated by ECGs for the purpose of creating of inexpensive screening tools. With additional validation and subsequent deployment, such screening tools may be useful for prioritized shunting of patients along appropriate pathways and improving outcomes.

Processing System

Figure 26:
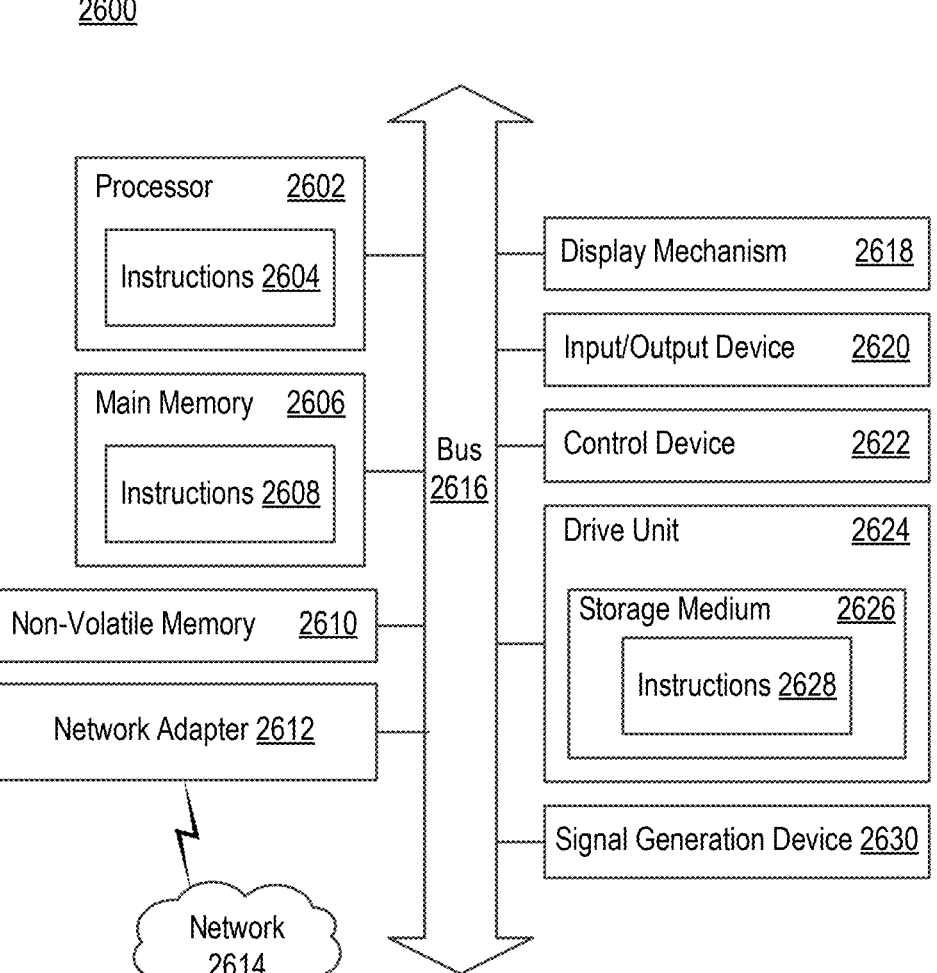
FIG. 26 is a block diagram illustrating an example of a processing system in which at least some operations described herein can be implemented.

FIG. 26 is a block diagram illustrating an example of a processing system 2600 in which at least some operations described herein can be implemented. For example, components of the processing system 2600 may be hosted on a computing device on which a diagnostic platform is stored and executed.

The processing system 2600 may include a processor 2602, main memory 2606, non-volatile memory 2610, network adapter 2612, display mechanism 2618, input/output device 2620, control device 2622 (e.g., a keyboard, pointing device, or mechanical input such as a button), drive unit 2624 that includes a storage medium 2626, or signal generation device 2630 that are communicatively connected to a bus 2616. The bus 2616 is illustrated as an abstraction that represents one or more physical buses and/or point-to-point connections that are connected by appropriate bridges, adapters, or controllers. The bus 2616, therefore, can include a system bus, Peripheral Component Interconnect (PCI) bus, PCI-Express bus, HyperTransport bus, Industry Standard Architecture (ISA) bus, Small Computer System Interface (SCSI) bus, Universal Serial Bus (USB), Inter-Integrated Circuit ($I^2C$) bus, or a bus compliant with Institute of Electrical and Electronics Engineers (IEEE) Standard 1394.

The processing system 2600 may share a similar computer processor architecture as that of a computer server, router, desktop computer, tablet computer, mobile phone, video game console, wearable electronic device (e.g., a watch or fitness tracker), network-connected ("smart") device (e.g., a television or home assistant device), augmented or virtual reality system (e.g., a head-mounted display), or another electronic device capable of executing a set of instructions (sequential or otherwise) that specify actions to be taken by the processing system 2600.

While the main memory 2606, non-volatile memory 2610, and storage medium 2626 are shown to be a single medium, the terms "storage medium" and "machine-readable medium" should be taken to include a single medium or multiple media that stores one or more sets of instructions 2626. The terms "storage medium" and "machine-readable medium" should also be taken to include any medium that is capable of storing, encoding, or carrying a set of instructions for execution by the processing system 2600.

In general, the routines executed to implement the embodiments of the present disclosure may be implemented as part of an operating system or a specific computer programs. Computer programs typically comprise one or more instructions (e.g., instructions 2604, 2608, 2628) set at various times in various memories and storage devices in a computing device. When read and executed by the processor 2602, the instructions cause the processing system 2600 to perform operations to execute various aspects of the present disclosure.

While embodiments have been described in the context of fully functioning computing devices, those skilled in the art will appreciate that the various embodiments are capable of being distributed as a program product in a variety of forms. The present disclosure applies regardless of the particular type of machine- or computer-readable medium used to actually cause the distribution. Further examples of machine- and computer-readable media include recordable-type media such as volatile memory and non-volatile memory 2610, removable disks, hard disk drives, optical disks (e.g., Compact Disk Read-Only Memory (CD-ROMS) and Digital Versatile Disks (DVDs)), cloud-based storage, and transmission-type media such as digital and analog communication links.

The network adapter 2612 enables the processing system 2600 to mediate data in a network 2614 with an entity that is external to the processing system 2600 through any communication protocol supported by the processing system 2600 and the external entity. The network adapter 2612 can include a network adaptor card, a wireless network interface card, a switch, a protocol converter, a gateway, a bridge, a hub, a receiver, a repeater, or a transceiver that includes a wireless chipset (e.g., enabling communication over Bluetooth or Wi-Fi).

Remarks

The foregoing description of various embodiments of the technology has been provided for the purposes of illustration and description. It is not intended to be exhaustive or to limit the claimed subject matter to the precise forms disclosed.

Many modifications and variation will be apparent to those skilled in the art. Embodiments were chosen and described in order to best describe the principles of the technology and its practical applications, thereby enabling others skilled in the relevant art to understand the claimed subject matter, the various embodiments, and the various modifications that are suited to the particular uses contemplated.

What is claimed is:

1. A method comprising:

accessing, by at least one computing device, transthoracic echocardiogram (TTE) data for a first plurality of patients, the TTE data comprising a plurality of echo reports, each containing text representing respective medical observations about right ventricular status or function of a respective one of the first plurality of patients;

applying, by the at least one computing device, a natural language processing (NLP) algorithm to the echo reports to identify indicators of the right ventricular status or function of the respective ones of the first plurality of patients;

assigning, by the at least one computing device, labels to the echo reports based on the identified indicators, wherein each of the labels specifies the right ventricular status and function of the respective ones of the first plurality of patients;

obtaining, by the at least one computing device, electrocardiogram (ECG) data comprising electrocardiogram waveforms for a second plurality of patients, the second plurality of patients comprising a third plurality of patients that are also included in the first plurality of patients;

matching, by the at least one computing device, the TTE data with the ECG data to identify data pairs of an echo report and an electrocardiogram waveform generated based on transthoracic cardiography and electrocardio-gramarformed within a predetermined interval of time for one of the third plurality of patients;

generating, by the at least one computing device, training data by labeling the electrocardiogram waveforms of the identified data pairs with labels assigned to the respective echo reports of the identified data pairs; and training, by the at least one computing device, a neural network model, using the training data, to predict right ventricular status or function of an individual from an electrocardiogram waveform of the individual.

2. The method of claim 1, wherein at least some of the labels are binary labels indicating whether the respective patient is positive for at least one of right ventricular systolic dysfunction (RVSD) or right ventricular dilation (RVD).

3. The method of claim 1, wherein at least some of the labels are multiclass labels indicating a severity of right ventricular dysfunction.

4. The method of claim 1, wherein at least some of the labels are multiclass labels indicating an outcome of interest.

5. The method of claim 4, wherein the outcome of interest is selected from the group consisting of at least one of: RVSD, RVD, and mitral regurgitation (MR).

6. The method of claim 1, wherein the TTE data further comprises left ventricular ejection fraction (LVEF) values abstracted from the echo reports, the method further comprising:

training a regression model, using training data comprising the electrocardiogram waveforms labeled with the LVEF values abstracted from the echo reports of the identified data pairs, to predict an LVEF value of an individual from an electrocardiogram waveform of the individual.

7. The method of claim 1, wherein the TTE data further comprises left ventricular ejection fraction (LVEF) values abstracted from the echo reports, the method further comprising:

stratifying the LVEF values into three clinically relevant ranges; and training a multiclass classification model, with training data comprising the electrocardiogram waveforms labeled with the stratified LVEF values abstracted from the echo reports of the identified data pairs, to predict an LVEF classification of an individual from an electrocardiogram waveform of the individual.

8. The method of claim 7, wherein the three clinically relevant ranges comprise a range of LVEF values no greater than 40%, a range of LVEF values greater than 40% and less than 50%, and a range of LVEF values greater than 50%.

9. The method of claim 1, wherein the TTE data further comprises LVEF values abstracted from the echo reports, the method further comprising:

prior to training the neural network model, discarding data with associated LVEF values above a first thresh-old and data with associated LVEF values below a second threshold that is lower than the first threshold.

10. The method of claim 1, wherein the neural network is a deep convolutional neural network.

11. A system comprising:

at least one computing device, configured by executing processing instructions stored on non-transitory pro-cessor readable media to perform steps, comprising:

accessing transthoracic echocardiogram (TTE) data for a first plurality of patients, the TTE data comprising a plurality of echo reports, each containing text repre-senting respective medical observations about right ventricular status or function of a respective one of the first plurality of patients;

applying a natural language processing (NLP) algorithm to the echo reports to identify indicators of the right ventricular status or function of the respective ones of the first plurality of patients;

assigning labels to the echo reports based on the identified indicators, wherein each of the labels specifies the right ventricular status and function of the respective ones of the first plurality of patients;

obtaining electrocardiogram (ECG) data comprising elec-trocardiogram waveforms for a second plurality of patients, the second plurality of patients comprising a third plurality of patients that are also included in the first plurality of patients;

matching the TTE data with the ECG data to identify data pairs of an echo report and an electrocardiogram wave-form generated based on transthoracic cardiography and electrocardiogramarformed within a predetermined interval of time for one of the third plurality of patients;

generating training data by labeling the electrocardiogram waveforms of the identified data pairs with labels assigned to the respective echo reports of the identified data pairs; and training a neural network model, using the training data, to predict right ventricular status or function of an individual from an electrocardiogram waveform of the individual.

12. The system of claim 11, wherein at least some of the labels are binary labels indicating whether the respective patient is positive for at least one of right ventricular systolic dysfunction (RVSD) or right ventricular dilation (RVD).

13. The system of claim 11, wherein at least some of the labels are multiclass labels indicating a severity of right ventricular dysfunction.

14. The system of claim 11, wherein at least some of the labels are multiclass labels indicating an outcome of interest.

15. The system of claim 14, wherein the outcome of interest is selected from the group consisting of at least one of: RVSD, RVD, and mitral regurgitation (MR).

16. The system of claim 11, wherein the TTE data further comprises left ventricular ejection fraction (LVEF) values abstracted from the echo reports, wherein the at least one computing device is further configured to perform steps, comprising:

training a regression model, using training data compris-ing the electrocardiogram waveforms labeled with the LVEF values abstracted from the echo reports of the identified data pairs, to predict an LVEF value of an individual from an electrocardiogram waveform of the individual.

17. The system of claim 11, wherein the TTE data further comprises left ventricular ejection fraction (LVEF) values abstracted from the echo reports, wherein the at least one computing device is further configured to perform steps, comprising:

stratifying the LVEF values into three clinically relevant ranges; and training a multiclass classification model, with training data comprising the electrocardiogram waveforms labeled with the stratified LVEF values abstracted from the echo reports of the identified data pairs, to predict an LVEF classification of an individual from an elec-trocardiogram waveform of the individual.

18. The system of claim 17, wherein the three clinically relevant ranges comprise a range of LVEF values no greater than 40%, a range of LVEF values greater than 40% and less than 50%, and a range of LVEF values greater than 50%.

19. The system of claim 11, wherein the TTE data further comprises LVEF values abstracted from the echo reports, wherein the at least one computing device is further configured to perform steps, comprising:

prior to training the neural network model, discarding data with associated LVEF values above a first threshold and data with associated LVEF values below a second threshold that is lower than the first threshold.

\* \* \* \* \*